(12) United States Patent
Okiyama

(10) Patent No.: US 8,556,879 B2
(45) Date of Patent: Oct. 15, 2013

(54) CONNECTOR

(75) Inventor: Tadashi Okiyama, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 231 days.

(21) Appl. No.: 13/121,882

(22) PCT Filed: Nov. 13, 2009

(86) PCT No.: PCT/JP2009/069391
§ 371 (c)(1),
(2), (4) Date: Mar. 30, 2011

(87) PCT Pub. No.: WO2010/061742
PCT Pub. Date: Jun. 3, 2010

(65) Prior Publication Data
US 2011/0175347 A1 Jul. 21, 2011

(30) Foreign Application Priority Data

Nov. 25, 2008 (JP) ................................. 2008-299993
Nov. 25, 2008 (JP) ................................. 2008-299994

(51) Int. Cl.
*A61J 1/00* (2006.01)
*A61J 1/10* (2006.01)
*A61J 1/20* (2006.01)
*A61M 5/32* (2006.01)

(52) U.S. Cl.
USPC ........... 604/411; 604/403; 604/405; 604/408; 604/415; 604/416

(58) Field of Classification Search
USPC ......... 604/411, 403, 404, 406, 407, 409, 412, 604/413, 414, 415, 416; 137/625.47
See application file for complete search history.

(56) References Cited

U.S. PATENT DOCUMENTS

| 4,397,335 | A | | 8/1983 | Doblar et al. | |
|---|---|---|---|---|---|
| 4,423,741 | A | * | 1/1984 | Levy | 600/581 |
| 4,534,758 | A | | 8/1985 | Akers et al. | |
| 4,759,756 | A | * | 7/1988 | Forman et al. | 604/413 |
| 4,972,876 | A | | 11/1990 | Kabata et al. | |
| 5,288,290 | A | | 2/1994 | Brody | |
| 5,466,220 | A | | 11/1995 | Brenneman | |
| 5,647,845 | A | | 7/1997 | Haber et al. | |
| 5,810,792 | A | * | 9/1998 | Fangrow et al. | 604/533 |
| 5,871,110 | A | | 2/1999 | Grimard et al. | |

(Continued)

FOREIGN PATENT DOCUMENTS

| CN | 101244297 | 8/2008 |
|---|---|---|
| JP | 56-95247 | 7/1981 |

(Continued)

*Primary Examiner* — Adam Marcetich
(74) *Attorney, Agent, or Firm* — Hamre, Schumann, Mueller & Larson, P.C.

(57) ABSTRACT

A connector (1) that can be connected to a first container and a second container (20) to transfer a liquid between the first container and the second container (20) includes a first connecting portion (3) that is engageable with the first container and a second connecting portion (4) that is engageable with the second container (20). The second connecting portion (4) is integrally provided with an engagement portion that is engageable with the second container (20) and a needle-like portion (7) for piercing into the second container (20). Thus, it is possible to prevent a container from falling off during liquid transfer. Also, since the needle-like portion (7) is integral with the second connecting portion (4), connection to the second container (20) is facilitated.

18 Claims, 32 Drawing Sheets

(56) References Cited

U.S. PATENT DOCUMENTS

| | | | |
|---|---|---|---|
| 6,193,675 B1 * | 2/2001 | Kraus et al. | 600/576 |
| 6,221,041 B1 | 4/2001 | Russo | |
| 2001/0029360 A1 | 10/2001 | Miyoshi et al. | |
| 2002/0017328 A1 | 2/2002 | Loo | |
| 2002/0095121 A1 * | 7/2002 | Norton et al. | 604/187 |
| 2002/0189712 A1 * | 12/2002 | Safabash | 141/329 |
| 2003/0023226 A1 | 1/2003 | Lopez | |
| 2003/0153895 A1 | 8/2003 | Leinsing | |
| 2004/0225274 A1 | 11/2004 | Jansen et al. | |
| 2004/0249341 A1 | 12/2004 | Newbrough et al. | |
| 2005/0033260 A1 | 2/2005 | Kubo et al. | |
| 2007/0079894 A1 | 4/2007 | Kraus et al. | |
| 2007/0088313 A1 * | 4/2007 | Zinger et al. | 604/403 |
| 2007/0244447 A1 * | 10/2007 | Capitaine et al. | 604/256 |
| 2007/0287953 A1 | 12/2007 | Ziv et al. | |
| 2008/0269680 A1 | 10/2008 | Ibranyan et al. | |
| 2009/0326506 A1 | 12/2009 | Hasegawa et al. | |
| 2010/0286606 A1 | 11/2010 | Ding | |
| 2011/0178493 A1 | 7/2011 | Okiyama | |

FOREIGN PATENT DOCUMENTS

| | | |
|---|---|---|
| JP | 62-189072 | 8/1987 |
| JP | 10-118158 | 5/1998 |
| JP | 2001-190689 | 7/2001 |
| JP | 2002-238979 | 8/2002 |
| JP | 2007-215775 | 8/2007 |
| WO | 2005/041846 | 5/2005 |
| WO | 2007/148708 | 12/2007 |

* cited by examiner

CONNECTOR

TECHNICAL FIELD

The present invention relates to a connector that can be interposed between containers to transfer a liquid, and particularly relates to a medical connector for transferring a liquid between, for example, a drug solution bag and a vial.

BACKGROUND ART

Drugs such as anticancer agents may be stored in the form of powder for storage stability and may be dissolved before use. In this case, a solvent is injected into a vial containing a drug, and a drug solution generated by dissolving the drug in the solvent is injected into a drug solution bag. Then, the drug solution in the drug solution bag is administered into the body via a tube attached to the drug solution bag. For example, the below-listed Patent Documents 1 and 2 propose devices for injecting a drug solution in the vial into the drug solution bag.

Patent Document 1 proposes that a mouth portion of a container (a vial) containing a drug is pierced with one end of a double-ended needle and a mouth portion of a container (a drug solution bag) containing a diluent is pierced with the other end of the double-ended needle, and in this state, a drug solution generated by dissolution in the drug-containing container is injected into the diluent-containing container.

Patent Document 2 proposes that a stopper of a glass bottle (a vial) is pierced with a bottle needle formed in a transfer device and a stopper of an empty bag (a drug solution bag) is pierced with a hollow needle, and in this state, a fluid contained in the glass bottle is transferred into the empty bag.

CITATION LIST

Patent Documents

Patent Document 1: JP 2002-238979A
Patent Document 2: JP S56-95247U

DISCLOSURE OF INVENTION

Problem to be Solved by the Invention

However, according to the devices proposed in Patent Documents 1 and 2, the device is connected to the vial by merely piercing the mouth portion of the vial with a needle portion that is integral with the device, and it is easy to detach the device from the vial. Thus, with the devices proposed in Patent Documents 1 and 2, there is a possibility that the vial easily may be detached from the device. Once the vial is detached from the device, leakage of the drug solution from the drug solution bag or leakage of the drug solution from the vial may occur.

The present invention has been made to solve conventional problems such as those described above, and it is an object thereof to provide a connector that prevents easy detachment of a connected container and prevents liquid leakage from the container.

Means for Solving Problem

In order to achieve the above-described object, a connector of the present invention is a connector that can be connected to a first container and a second container to transfer a liquid between the first container and the second container, the connector including a first connecting portion that is engageable with the first container and a second connecting portion that is engageable with the second container, wherein the second connecting portion is integrally provided with an engagement portion that is engageable with the second container and a needle-like portion for piercing into the second container.

Effects of the Invention

With the connector of the present invention, it is possible to prevent easy detachment of a connected container and prevent liquid leakage from the container.

DESCRIPTION OF THE INVENTION

Figure 1:
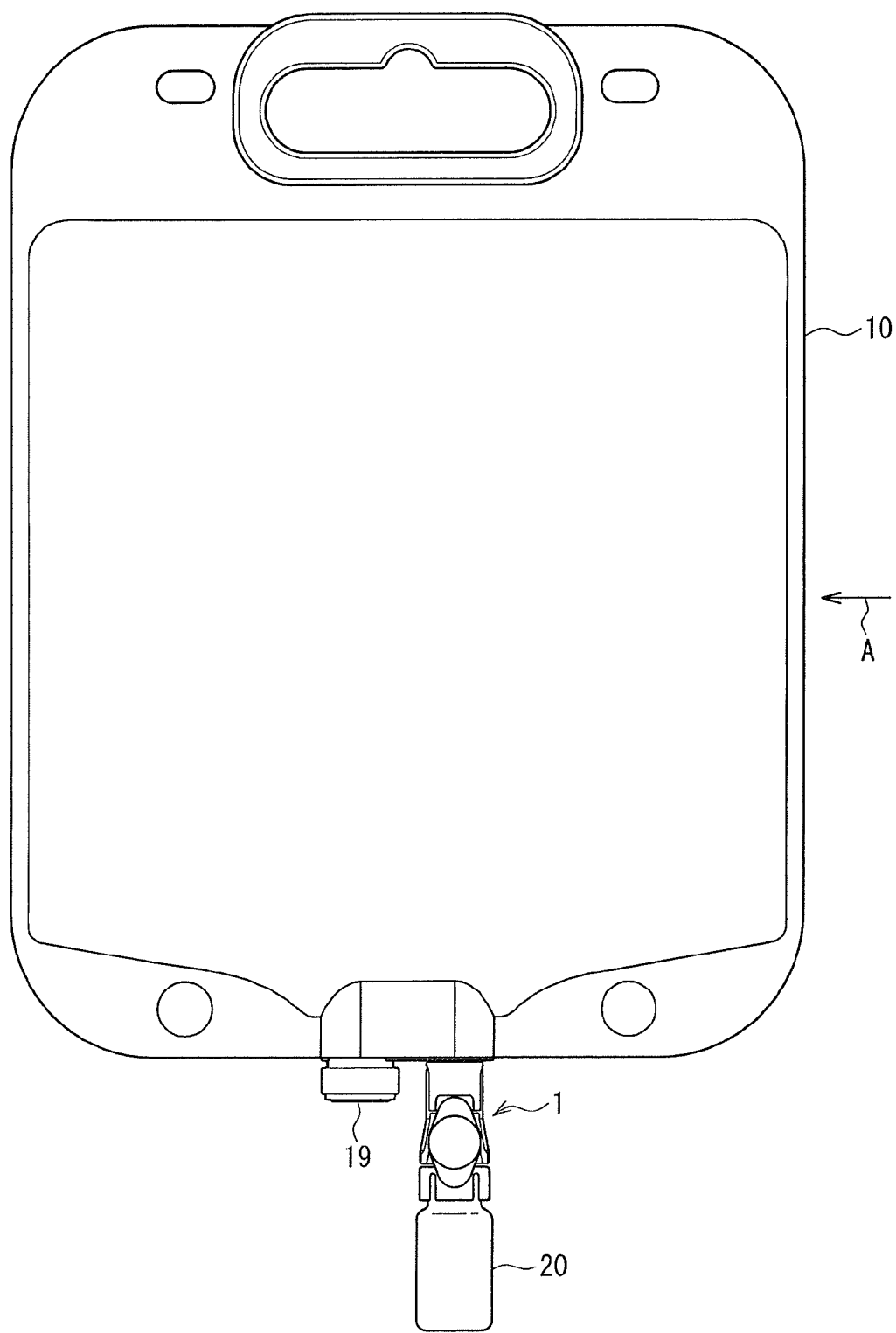
FIG. 1 is a diagram showing an example of use of a connector 1 according to Embodiment 1 of the present invention.

According to the present invention, since liquid transfer between containers can be performed in a state in which the first and the second containers are engaged with the connector, the containers can be prevented from falling off during the liquid transfer. In particular, since the engagement portion and the needle-like portion of the second connecting portion are integral with each other, easy detachment of the second container can be prevented, and also connection to the second container is facilitated.

In the connector of the present invention, it is preferable that the first connecting portion includes a releasing mechanism for releasing engagement with the first container and the second connecting portion includes no releasing mechanism for releasing engagement with the second container. This configuration can prevent easy detachment of the second container while facilitating detachment of the first connecting portion from the first container. Thus, when the second container is to be disposed of, a working procedure for detaching the second container integrally with the connector is performed readily, and leakage of the contents of the second container that would be caused by detachment of the second container alone can be prevented.

Moreover, it is preferable that the engagement portion of the second connecting portion is a hollow cylindrical connecting port that is engageable with a mouth portion of the second container, and the connecting port has a protrusion protruding from an inner circumferential surface of the connecting port. With this configuration, the second connecting portion is engaged more reliably with the second container, and this is more advantageous in preventing the second container from falling off.

Moreover, it is preferable that the connecting port has a slit that is cut in a side face of the connecting port. This configuration facilitates engagement of the second connecting portion with the second container.

Moreover, it is preferable that the first connecting portion is integrally provided with a lever lock having a claw portion that is engageable with a portion of the first container, the lever lock doubles as a releasing mechanism for releasing engagement with the first container, and engagement of the lever lock with the first container is released by bending the lever lock. With this configuration, attachment and detachment of the first connecting portion readily are performed by opening and closing of a lever portion of the lever lock.

Moreover, it is preferable that the first connecting portion is a rotary lock, the rotary lock has a recessed groove that is engageable with a projection formed on the first container, the rotary lock doubles as a releasing mechanism for releasing engagement with the first container, and engagement between the projection and the recessed groove is released by rotating the rotary lock around an axis thereof. This configuration also facilitates attachment and detachment of the first connecting portion. Moreover, even though releasing of engagement of the first connecting portion with the first container is facilitated, inadvertent releasing can be prevented because it is necessary to rotate the rotary lock to release the engagement.

Moreover, it is preferable that the connector further includes a syringe that includes a cylinder and a movable piston, wherein a liquid is transferred between the first container and the second container by ejecting and drawing in air by moving the piston. With this configuration, it is possible to eject and draw in air by a simple operation, and this facilitates liquid transfer between containers and also facilitates adjustment of the amount of air to be ejected and the amount of air to be drawn in.

Moreover, it is preferable that the connector further includes a dropper that can expand and contract, wherein a liquid is transferred between the first container and the second container by ejecting and drawing in air by expanding and contracting the dropper. With this configuration, it is possible to eject and draw in air with a simple structure and by a simple operation, and this facilitates liquid transfer between containers.

Moreover, it is preferable that the connector further includes a hydrophobic filter, wherein air is ejected and drawn in through the hydrophobic filter. With this configuration, it is possible to prevent the liquid from flowing into the cylinder or the dropper.

Moreover, it is preferable that the first connecting portion has a portion covered with a shield that can open and close by extension and retraction. With this configuration, liquid leakage from the first connecting portion can be prevented even after the first connecting portion has been detached from the first container. Therefore, if the second container is disposed of in a state in which the second connecting portion and the second container remain in the connected state, liquid leakage from the second container will be prevented.

Moreover, it is preferable that the connector includes a connector main body provided with a tubular portion and a stopcock that is fitted in the tubular portion so as to be rotatable around an axis of the tubular portion, wherein one end of the tubular portion is sealed with the stopcock that is fitted in the tubular portion; an open portion is formed at the other end of the tubular portion; a penetrating flow channel that passes through the stopcock in a radial direction thereof is formed in the stopcock; a first hole, a second hole, a third hole, and a fourth hole are formed in the connector main body; the first, the second, the third, and the fourth holes are holes that bring an inner space of the tubular portion into communication with an external space of the connector main body; a flow channel that brings an opening formed on the open portion side into communication with an opening formed in a side face of the stopcock is formed in the stopcock; and switching between a setting that brings the first hole into communication with the flow channel in the stopcock and brings the third hole into communication with the fourth hole via the penetrating flow channel and a setting that brings the second hole into communication with the flow channel in the stopcock and brings the third hole into communication with the fourth hole via the penetrating flow channel can be achieved by rotating the stopcock.

With this configuration, when the syringe, the drug solution bag, and the vial are connected to the connector, it is possible to transfer a liquid between the vial and the drug solution bag via the syringe by switching between the flow channel settings within the connector, and it is also possible accurately to adjust the amount of the liquid to be transferred. Thus, a required amount of drug solution can be injected into the drug solution bag with precision.

In the connector of the present invention, it is preferable that the first connecting portion and the second connecting portion are provided in the connector main body; connecting ports are formed in the first and the second connecting portions; the first and the third holes are in communication with a space in the first connecting portion; and the second and the fourth holes are in communication with a space on the connecting port side of the second connecting portion. This configuration facilitates connection of the connector to the drug solution bag and the vial.

Moreover, it is preferable that the first connecting portion includes a lever lock that is integral with the connecting port formed in the first connecting portion. This configuration facilitates attachment and detachment of the first connecting portion.

Moreover, it is preferable that the second connecting portion has a protrusion protruding from an inner circumferential surface of the connecting port formed in the second connecting portion. With this configuration, it is possible to prevent the second connecting portion from falling off.

Moreover, it is preferable that the first connecting portion has a portion covered with a shield that can open and close by extension and retraction. With this configuration, leakage of the drug solution from the first connecting portion can be prevented even after the first connecting portion has been detached from the drug solution bag. Therefore, if the vial is disposed of in a state in which the second connecting portion and the vial remain in the connected state, leakage of the drug in the vial will be prevented.

Moreover, it is preferable that a graduated syringe including a cylinder and a movable piston is integrally formed on the other end side of the tubular portion. This configuration facilitates assembly of the connector prior to operation. Moreover, erroneous detachment of the syringe and resulting opening of the other end of the tubular portion can be prevented.

Moreover, it is preferable that a lever extended from the stopcock is formed on the stopcock, and the lever is disposed in such a manner that when the stopcock is set to the setting that brings the first hole into communication with the flow channel in the stopcock, a leading end of the extended lever points to an external space side communicating with the first hole, and when the stopcock is set to the setting that brings the second hole into communication with the flow channel in the stopcock, the leading end of the extended lever points to an external space side communicating with the second hole. With this configuration, it is possible to determine the status of the flow channel setting within the connector from the orientation of the lever.

Moreover, it is preferable that a hydrophobic filter is provided in at least one of the third hole, the penetrating flow channel, and the fourth hole. With this configuration, when the syringe, the drug solution bag, and the vial are connected to the connector, liquid transfer between the drug solution bag and the vial via the third hole, the penetrating flow channel, and the fourth hole can be prevented reliably. This also renders accurate adjustment of the amount of liquid to be transferred between the vial and the drug solution bag via the syringe more reliable.

Hereinafter, embodiments of the present invention will be described with reference to the drawings.

Embodiment 1

FIG. 1 is a diagram showing an example of the use of a connector 1 according to Embodiment 1 of the present invention. In the example in this diagram, a drug solution bag 10 serving as a first container and a vial 20 serving as a second container are connected to each other via the connector 1.

Figure 5:
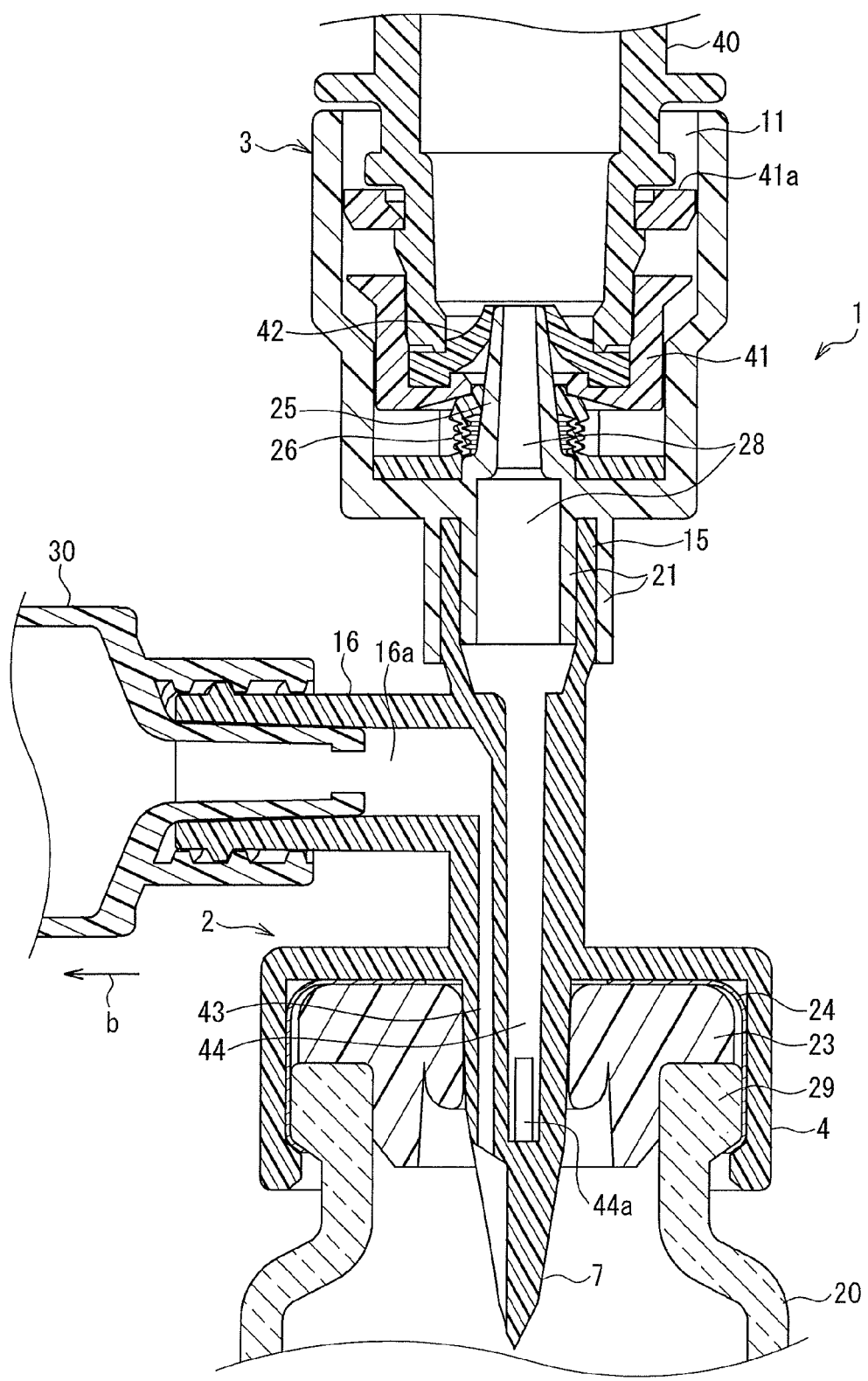
FIG. 5 is a cross-sectional view of the connector 1 according to Embodiment 1 of the present invention.

In the following description, components that are attached to the drug solution bag 10, such as a connecting port 40 and a port portion 41 in FIG. 5, are denoted separately from the drug solution bag 10 for convenience of description. However, such components are components that constitute the drug solution bag 10. Therefore, even though a first connecting portion 3 is engaged with the port portion 41 in FIG. 5, this means that the first connecting portion 3 is engaged with the drug solution bag 10.

Similarly, in FIG. 5, a rubber stopper 23 and a cap 24 that are attached to the vial 20 are components that constitute the vial 20. With respect to the illustration in FIG. 5, although it is both possible to regard a second connecting portion 4 as being engaged with the cap 24 and to regard this connecting portion as being engaged with a mouth portion 29 of the vial 20, the fact remains that this connecting portion is engaged with the vial 20.

The drug solution bag 10 is formed by shaping a soft resin sheet into a pouch-like shape. The drug solution bag 10 can be formed by, for example, superposing two resin sheets over each other and joining their peripheral edge portions together by heat welding or the like. The vial 20 is a container containing a drug and is, for example, a glass bottle whose mouth portion is sealed with a rubber stopper and a cap.

Figure 2:
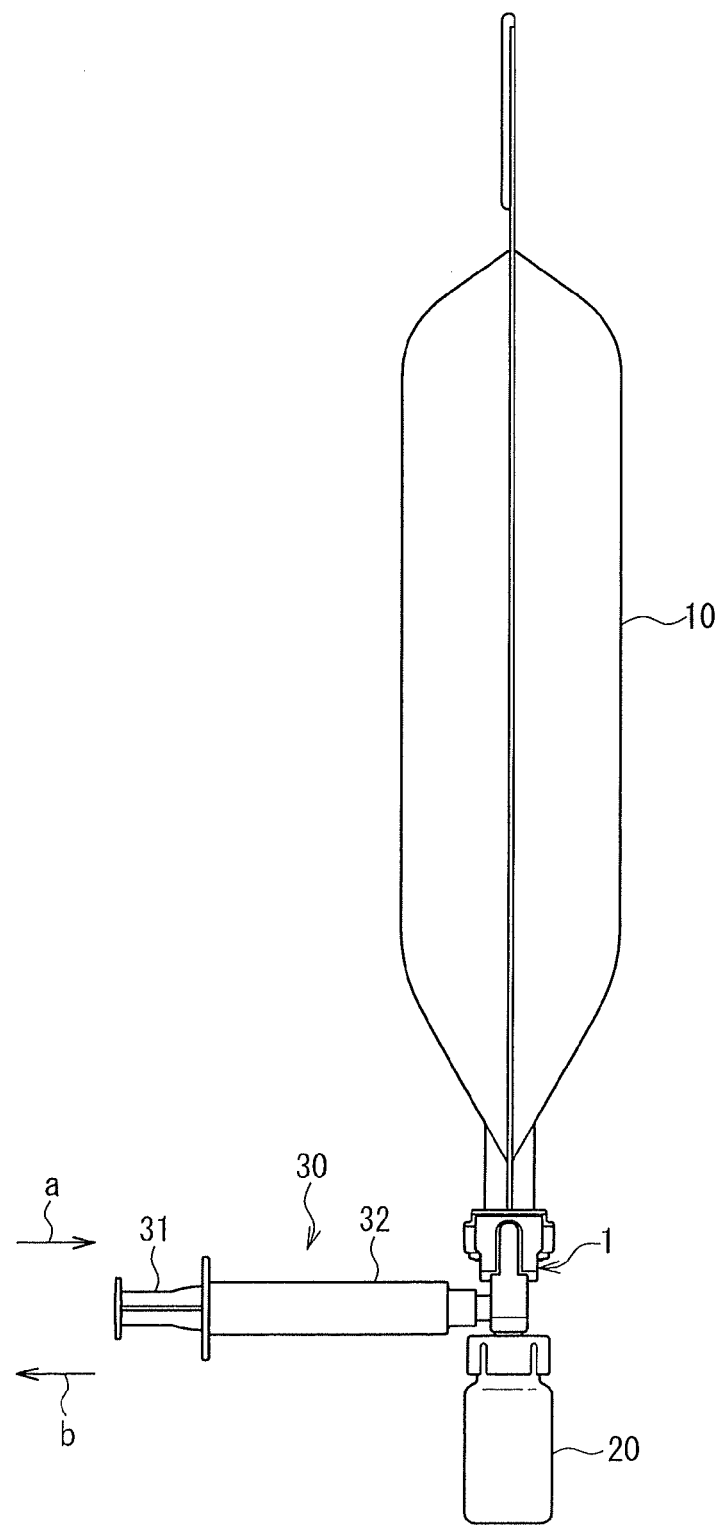
FIG. 2 is a diagram showing the example in FIG. 1 as seen from the direction of arrow A.

FIG. 2 shows the example in FIG. 1 as seen from the direction of arrow A. A syringe 30 is attached to the connector 1. The syringe 30 includes a hollow cylindrical cylinder 32 and a movable piston 31. Pushing the piston 31 in the direction of arrow "a" can cause air in the cylinder 32 to be ejected from a leading end of the cylinder 32. On the other hand, pulling the piston 31 in the direction of arrow "b" can cause air to be drawn into the cylinder 32.

Figure 3:
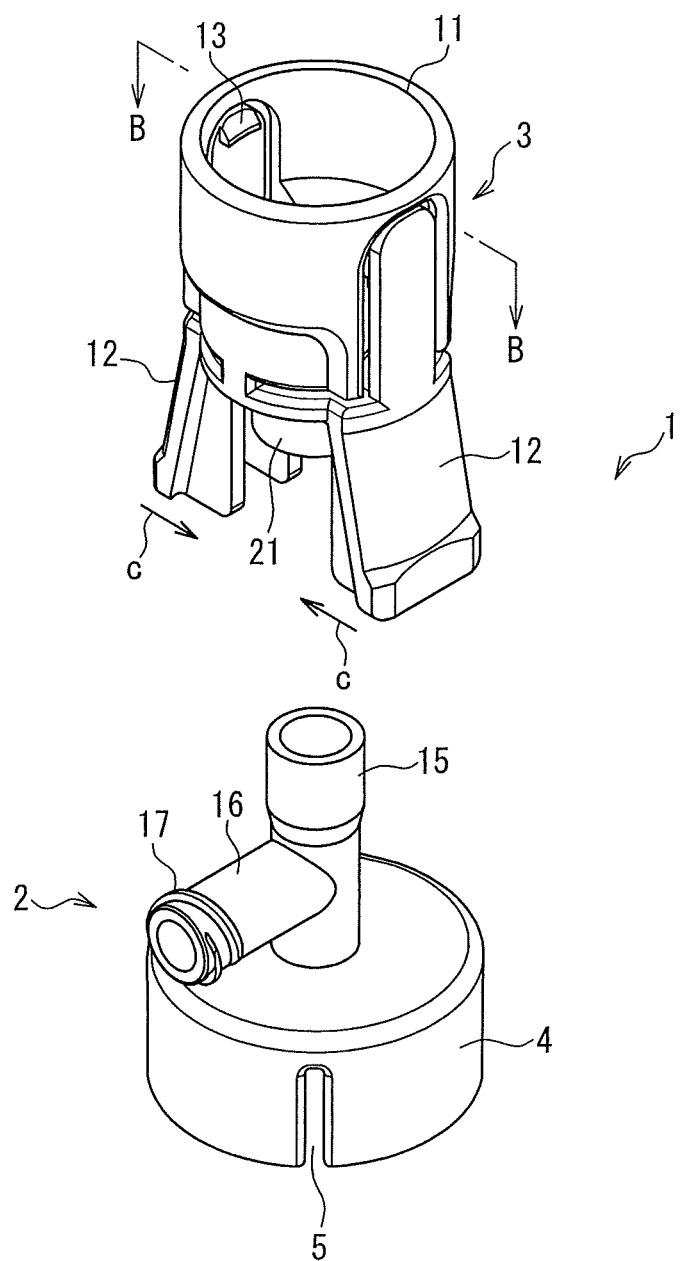
FIG. 3 is an exploded perspective view of the connector 1 according to Embodiment 1 of the present invention.

FIG. 3 is an exploded perspective view of the connector 1. As shown in FIG. 3, the connector 1 can be disassembled into a connector main body 2 and the first connecting portion 3. The connector main body 2 is integral with the second connecting portion 4.

The first connecting portion 3 is provided integrally with a hollow cylindrical connecting port 11 and lever locks 12. The first connecting portion 3 is a connector for connecting the connector 1 to the drug solution bag 10 (FIG. 1). During connection to the drug solution bag 10, the hollow cylindrical port portion 41 (FIG. 7) fixed to the drug solution bag 10 is inserted into the connecting port 11.

At this time, while lower portions of the lever locks 12 are bent in the direction of arrow "c", claw portions 13 of the lever locks 12 engage an end face 41a (FIGS. 7 and 8) of the port portion 41. Details of the connection of the first connecting portion 3 to the drug solution bag 10 will be described later with reference to FIGS. 7 and 8.

The connector main body 2 includes an axial tubular portion 15 and a horizontal tubular portion 16 intersecting with each other. A thread 17 is formed on the horizontal tubular portion 16 for the purpose of screwing to the syringe 30 (FIG. 2). The connector 1, in a connected state as shown in FIG. 2, allows liquid transfer between the drug solution bag 10 and the vial 20 by moving the piston 31. The liquid transfer will be described later with reference to FIGS. 5 and 6.

Figure 4:
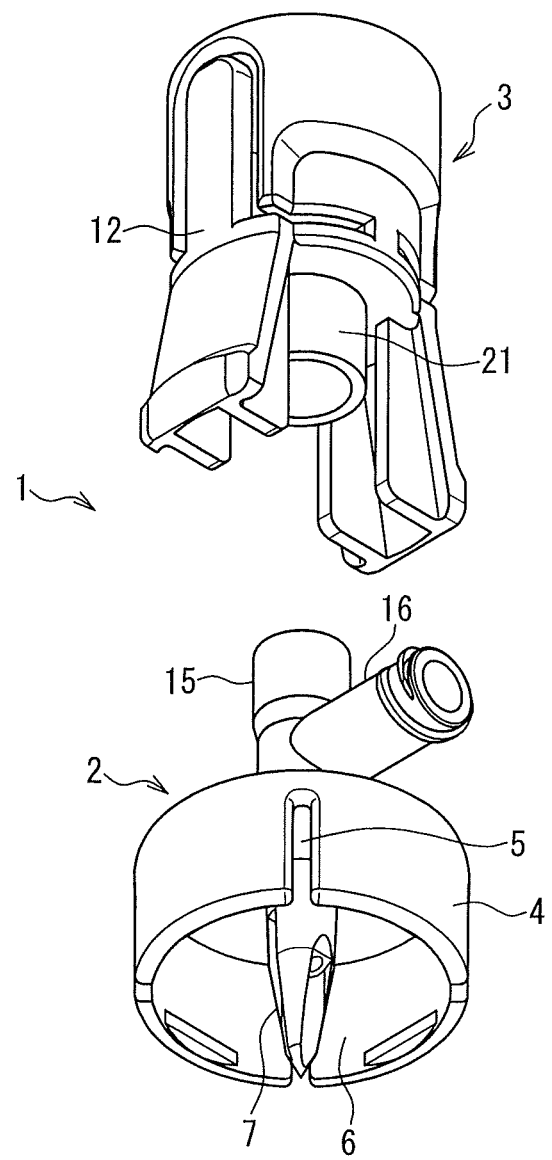
FIG. 4 is an exploded perspective view of the connector 1 in FIG. 3 as seen from a different angle from that of FIG. 3.

FIG. 4 is an exploded perspective view of the connector 1 as seen from a different angle from that of FIG. 3. FIG. 4 shows a back side of the first connecting portion 3 and the connector main body 2. A connecting tubular portion 21 is formed on the back side of the first connecting portion 3. The first connecting portion 3 can be connected to the connector main body 2 by fitting this connecting tubular portion 21 to the axial tubular portion 15 of the connector main body 2.

The second connecting portion 4 is provided integrally with a hollow cylindrical connecting port 6 and a needle-like portion 7. The second connecting portion 4 is for connecting the connector main body 2 to the vial 20. The connecting port 6 serves as an engagement portion that is engageable with the mouth portion 29 (FIG. 5) of the vial 20. The needle-like portion 7 has a sharp tip, and the rubber stopper 23 (FIG. 5) of the vial 20 can be pierced with the needle-like portion 7.

During connection of the second connecting portion 4 to the vial 20, while the rubber stopper 23 (FIG. 5) of the vial 20 is pierced with the needle-like portion 7, the mouth portion 29 of the vial 20 is engaged in the connecting port 6 of the second connecting portion 4. Details of this connection will be described later with reference to FIGS. 9 and 10.

Figure 7:
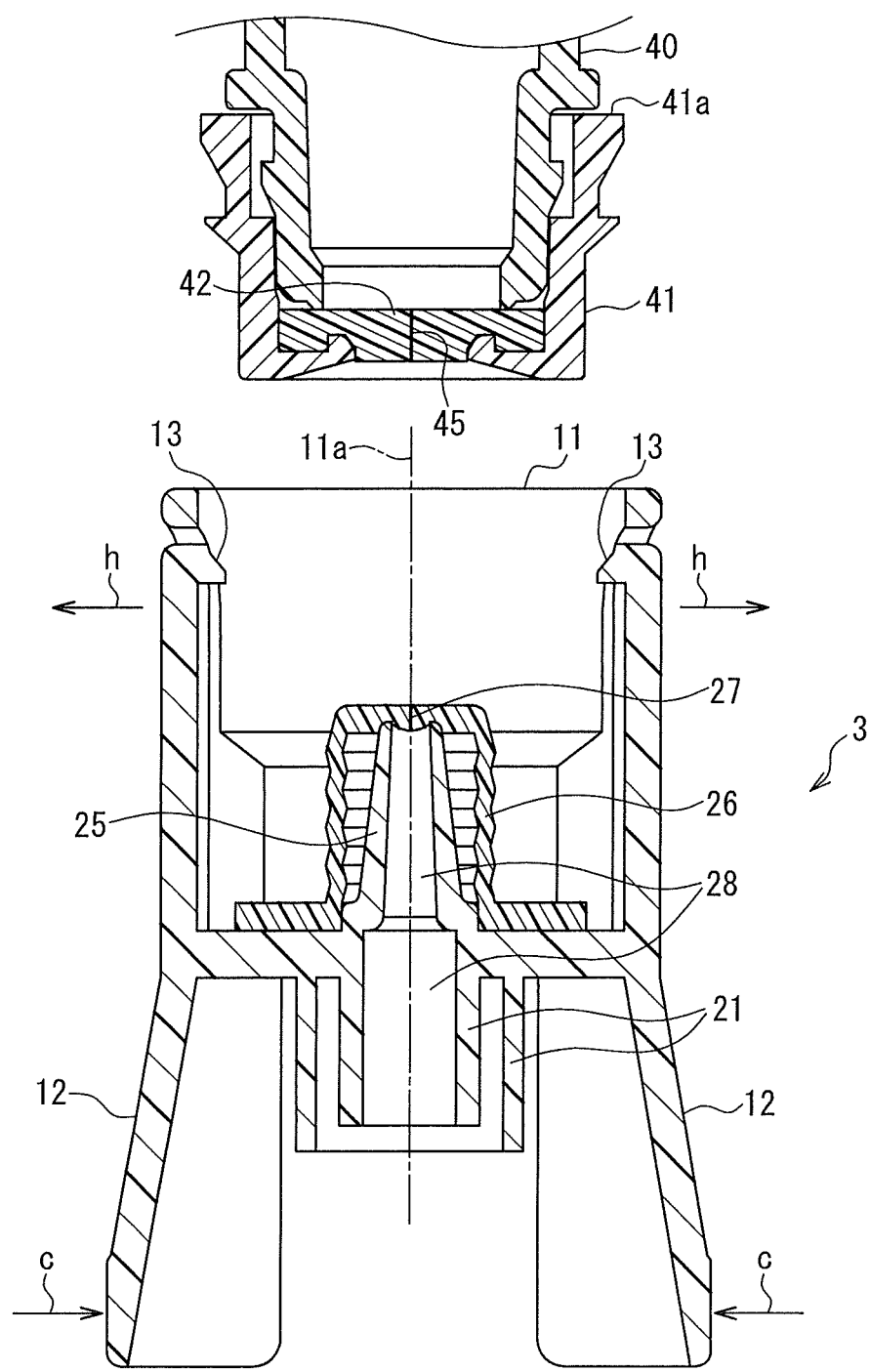
FIG. 7 is a cross-sectional view showing a state before a first connecting portion 3 according to Embodiment 1 of the present invention is connected to the drug solution bag 10.
Figure 8:
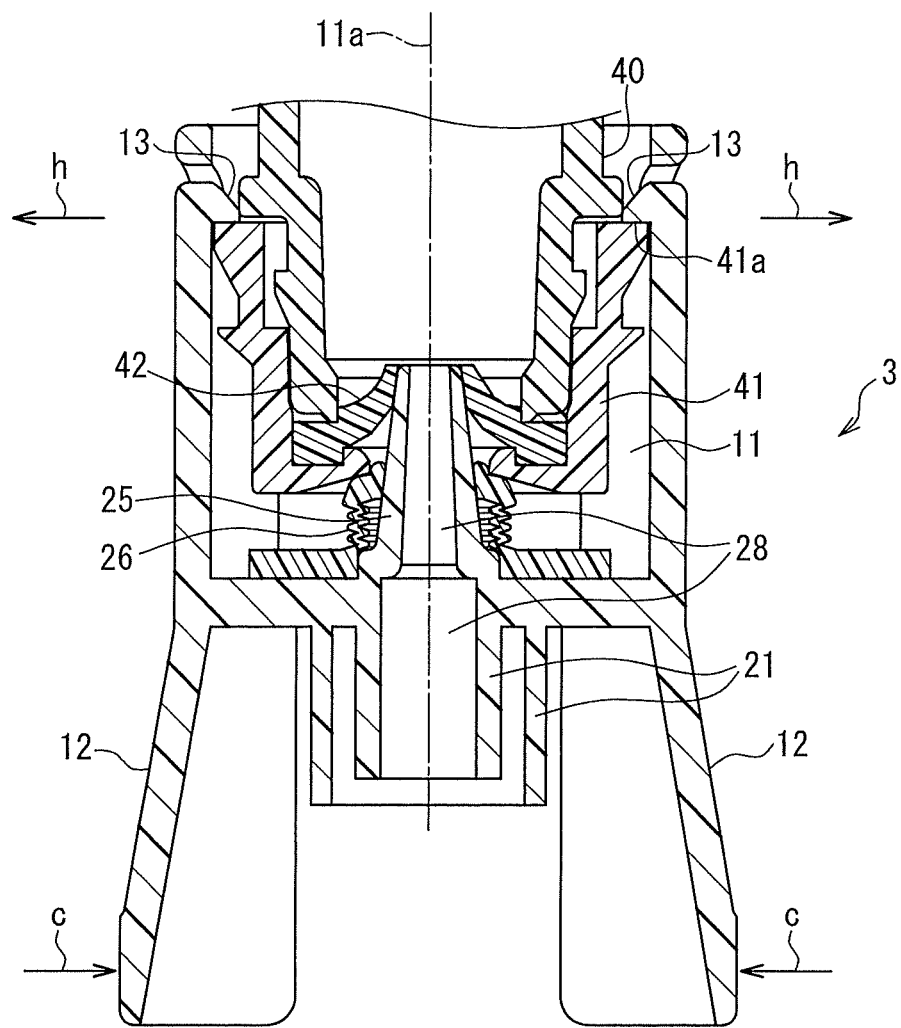
FIG. 8 is a cross-sectional view showing a state in which the first connecting portion 3 according to Embodiment 1 of the present invention has been connected to a port portion 41.

FIG. 5 shows a cross-sectional view of the connector 1. This cross-sectional view corresponds to a vertical cross-sectional view of the connector 1 and its peripheral portions shown in FIG. 2. The port portion 41 is attached to a leading end portion of the connecting port 40 attached to the drug solution bag 10. The port portion 41 is inserted in the connecting port 11 of the first connecting portion 3. Although not shown in this cross-sectional view, the claw portions 13 (FIG. 3) of the lever locks 12 that are integral with the first connecting portion 3 are engaged with the end face 41a of the port portion 41 to connect the first connecting portion 3 to the port portion 41 (FIG. 8). As described above, details of this connection will be described later with reference to FIGS. 7 and 8.

The first connecting portion 3 has an upright tubular portion 25 formed in a central portion of the connecting port 11. A leading end portion of the upright tubular portion 25 pushes up a septum (a partition) 42 attached to the port portion 41. The septum 42 is made of a soft material, and a slit is formed therein. In the state shown in FIG. 5, the leading end portion of the upright tubular portion 25 forces the slit of the septum 42 open by pushing up the septum 42. Thus, an inner space of the connecting port 40 is in communication with inner spaces 28 of the upright tubular portion 25 and the connecting tubular portion 21.

The connecting tubular portion 21 of the first connecting portion 3 is fitted to the axial tubular portion 15 of the connector main body 2. Thus, the first connecting portion 3 is connected to the connector main body 2.

A first flow channel 43 and a second flow channel 44 are formed in the connector main body 2. The first flow channel 43 is a flow channel that brings an inner space 16a of the horizontal tubular portion 16 into communication with an external space of the connector main body 2. The second flow channel 44 is a flow channel that brings the inner spaces 28 of the upright tubular portion 25 and the connecting tubular portion 21 into communication with the external space of the connector main body 2.

The mouth portion 29 of the vial 20 is sealed with the rubber stopper 23 and the cap 24. The rubber stopper 23 is press-fitted in an opening of the vial 20. The cap 24 is formed by, for example, processing a sheet metal, and covers the mouth portion 29 of the vial 20. As shown in FIG. 5, the vial 20 and the connector main body 2 are connected to each other by the second connecting portion 4. Details of this connection will be described later with reference to FIGS. 9 and 10.

Hereinafter, an operating procedure during injection of a drug in the vial 20 into the drug solution bag 10 will be described with reference to FIGS. 5 and 6.

In FIG. 5, by pulling the piston 31 (FIG. 2) of the syringe 30 in the direction of arrow "b", air in the vial 20 can be drawn into the inner space 16a of the horizontal tubular portion 16 and further into the syringe 30. Thus, a solvent in the drug solution bag 10 is injected into the vial 20 through the inner spaces 28 of the upright tubular portion 25 and the connecting tubular portion 21, the second flow channel 44, and an opening 44a.

Once the solvent is injected into the vial 20, the drug in powder form contained in the vial 20 is dissolved in the solvent. It is possible to accelerate the dissolution by shaking the vial 20.

Figure 6:
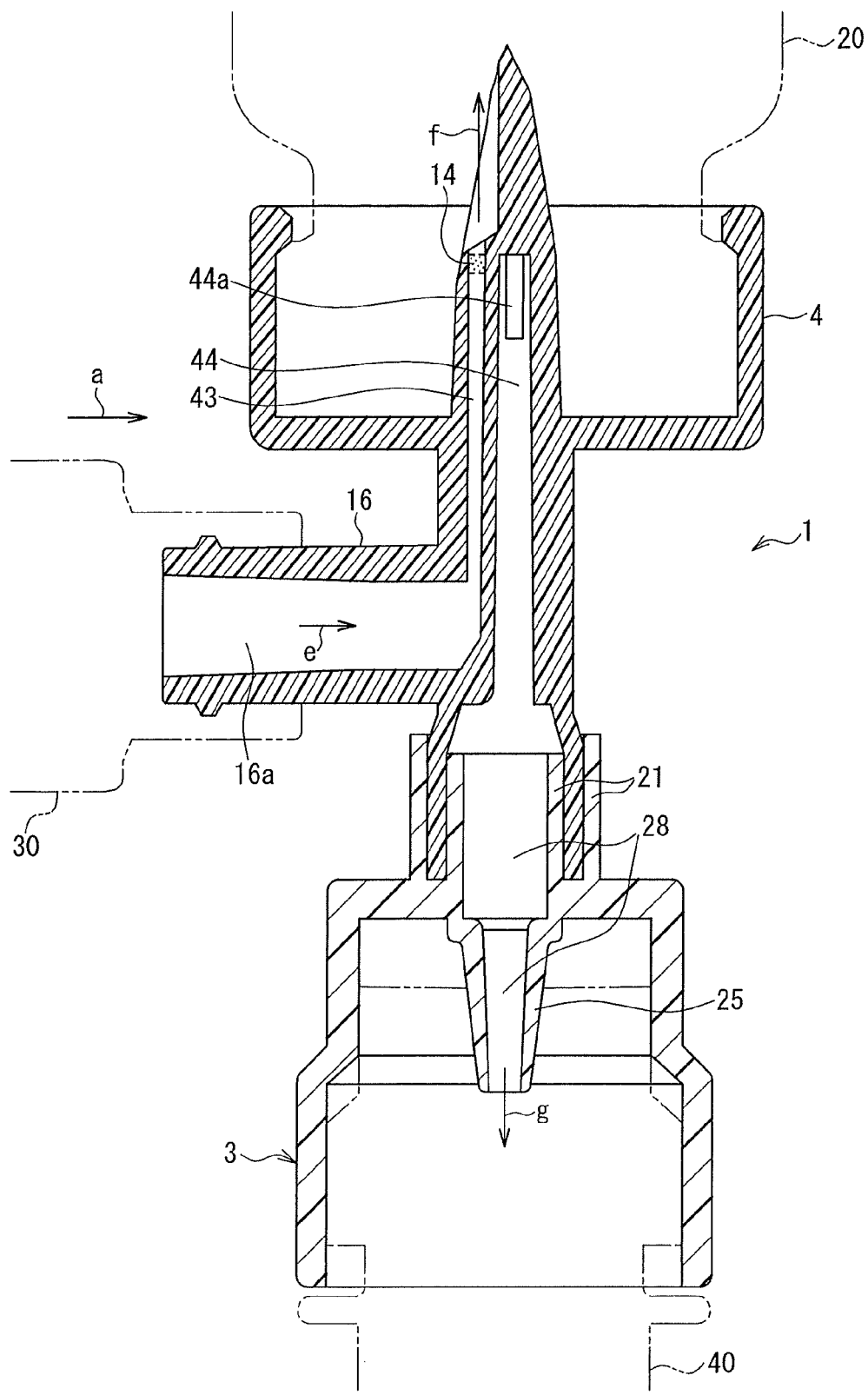
FIG. 6 is a cross-sectional view showing a state in which a drug solution that has been generated within a vial 20 by dissolving a drug in powder form is injected into a drug solution bag 10, according to Embodiment 1 of the present invention.

FIG. 6 is a cross-sectional view showing a state in which a drug solution that has been generated within the vial 20 by dissolving the drug in powder form is injected into the drug solution bag 10. For clarity of illustration, the connecting port 40, the port portion 41, the syringe 30, and the vial 20 in FIG. 5 are shown simplified in chain double-dashed lines.

In FIG. 6, the vertical relationship between the connecting port 40 of the drug solution bag 10 and the vial 20 is inverted with respect to that shown in FIG. 5. That is to say, in FIG. 5, the vial 20 is positioned on the lower side, whereas in FIG. 6, the vial 20 is positioned on the upper side.

In the state shown in FIG. 6, when the piston 31 (FIG. 2) of the syringe 30 is pushed in the direction of arrow "a", air in the syringe 30 is expelled into the inner space 16a of the horizontal tubular portion 16. The air that has reached the inner space 16a flows in the direction of arrow "e" and passes through the first flow channel 43 to be injected into the vial 20 as indicated by arrow "f".

Thus, the drug solution in the vial 20 flows out through the opening 44a, the second flow channel 44, and the inner spaces 28 of the upright tubular portion 25 and the connecting tubular portion 21 toward the inside of the drug solution bag 10 as indicated by arrow "g".

When the injection amount into the drug solution bag 10 is to be increased, the piston 31 (FIG. 2) that has been once pushed can be withdrawn, and the piston 31 can be again pushed in the direction of arrow "a". In this case, there is a possibility that the drug solution in the vial 20 may be drawn into the syringe 30 during withdrawal of the piston 31. In order to prevent such an inflow of the drug solution into the syringe 30, a hydrophobic filter 14 can be disposed in the first flow channel 43 as shown in FIG. 6.

The hydrophobic filter 14 has air permeability and allows air, but not liquid, to pass through. Therefore, it is possible to prevent the drug solution in the vial 20 from flowing into the syringe 30 during withdrawal of the piston 31.

It should be noted that although FIG. 6 shows an example in which the hydrophobic filter 14 is disposed in the first flow channel 43, the hydrophobic filter 14 can be disposed anywhere in a space from a leading end of the first flow channel 43 to the syringe 30, and may be provided in the inner space 16a of the horizontal tubular portion 16.

The drug solution in the vial 20 can be injected into the drug solution bag 10 through the process as described above. The drug solution in the drug solution bag 10 will be administered into the body via a tube with a needle with which a port portion 19 (FIG. 1) is pierced.

The present embodiment is described using an example in which the syringe 30 (FIG. 2) and the connector main body 2 are separate components. However, a configuration in which the cylinder portion 32 of the syringe 30 and the connector main body 2 are integral with each other also may be employed. For the cylinder portion 32 and the connector main body 2 to be integral with each other, the cylinder portion 32 may be molded integrally with the horizontal tubular portion 16 (FIG. 3), or the cylinder portion 32 may be fixed to the horizontal tubular portion 16 (FIG. 3) with an adhesive. This configuration eliminates the need for attachment of the syringe 30 and thus facilitates assembly of the connector 1 prior to operation. Moreover, erroneous detachment of the syringe 30 and resulting opening of a non-intersecting end of the horizontal tubular portion 16 can be prevented.

Next, a structure for connecting the first connecting portion 3 to the drug solution bag 10 will be described with reference to FIGS. 7 and 8. FIG. 7 is a cross-sectional view showing a state before the first connecting portion 3 is connected to the drug solution bag 10. As described above, the connecting port 40 is attached to the drug solution bag 10. The port portion 41 is attached to the leading end portion of the connecting port 40. The septum (the partition) 42 in which a slit 45 is formed is attached to the port portion 41. The first connecting portion 3 shown in FIG. 7 corresponds to a cross-sectional view taken along line BB in FIG. 3. The lever locks 12 are integral with the first connecting portion 3.

FIG. 8 is a cross-sectional view showing a state in which the first connecting portion 3 has been engaged with and connected to the port portion 41. The port portion 41 is inserted in the connecting port 11, and also the claw portions 13 of the lever locks 12 are engaged with the end face 41a of the port portion 41. During insertion of the port portion 41 into the connecting port 11, in FIG. 7, while the lower portions of the lever locks 12 are bent toward a central axis 11a of the connecting port 11 (the direction of arrow "c"), the claw portions 13 of the ever locks 12 are displaced away from the central axis 11a of the connecting port 11 (the direction of arrow "h"). At the point in time when insertion of the port portion 41 into the connecting port 11 has been completed, the claw portions 13 are in engagement with the end face 41a of the port portion 41 as shown in FIG. 8.

Here, in FIG. 7, the upright tubular portion 25 that is integral with the first connecting portion 3 is covered with a shield 26 that can open and close by extension and retraction. A slit 27 is formed in the shield 26. When the shield 26 is retracted, a portion where the slit 27 is formed opens (FIG. 8), and when the retracted shield 26 is restored, the portion where the slit 27 is formed closes (FIG. 7).

In the state shown in FIG. 7, the shield 26 covers the upright tubular portion 25, whereas in the state shown in FIG. 8, the shield 26 is retracted, and the upright tubular portion 25 extends outside the shield 26. This is because during insertion of the port portion 41 into the connecting port 11, a lower portion of the port portion 41 presses against the shield 26 such that the shield is pushed down.

A leading end portion of the upright tubular portion 25 extending outside the shield 26 pushes up the septum 42 attached to the port portion 41 and thus forces the slit 45 (FIG. 7) of the septum 42 open. As a result, the inner space of the connecting port 40 is brought into communication with the inner spaces 28 of the upright tubular portion 25 and the connecting tubular portion 21.

Next, after a required amount of the drug solution has been injected into the drug solution bag 10, the first connecting portion 3 that is integral with the vial 20 is to be detached from the port portion 41. During detachment, in FIG. 8, the lower portions of the lever locks 12 can be pressed toward the central axis 11a of the connecting port 11 (the direction of arrow "c"), and the claw portions 13 of the lever locks 12 displaced away from the central axis 11a of the connecting port 11 (the direction of arrow "h").

The first connecting portion 3 returns to the state shown in FIG. 7 after being detached from the port portion 41. In the state shown in FIG. 7, the retracted shield 26 has been restored and covers the upright tubular portion 25 again. In this state, leakage of the drug solution in the vial 20 is prevented.

It should be noted that, in FIG. 7, the structure of the upright tubular portion 25 covered with the shield 26 may be provided on the port portion 41 side. In this case, the structure in which the opening is covered with the septum 42 that can open and close by extension and retraction will be provided in the first connecting portion 3. According to this configuration, in FIG. 7, although the vertical relationship between the upright tubular portion 25 and the septum 42 is inverted, the fact remains that the inner space of the connecting port 40 and the inner space 28 of the connecting tubular portion 21 are brought into communication with each other.

Moreover, the first connecting portion 3 of the present embodiment is merely an example, and various types of connecting systems can be employed. Furthermore, although an example in which the first connecting portion 3 and the connector main body 2 are configured as separate components has been described, a configuration in which the first connecting portion 3 and the connector main body 2 are integrally molded is conceivable depending on the structure of the first connecting portion 3.

Figure 9:
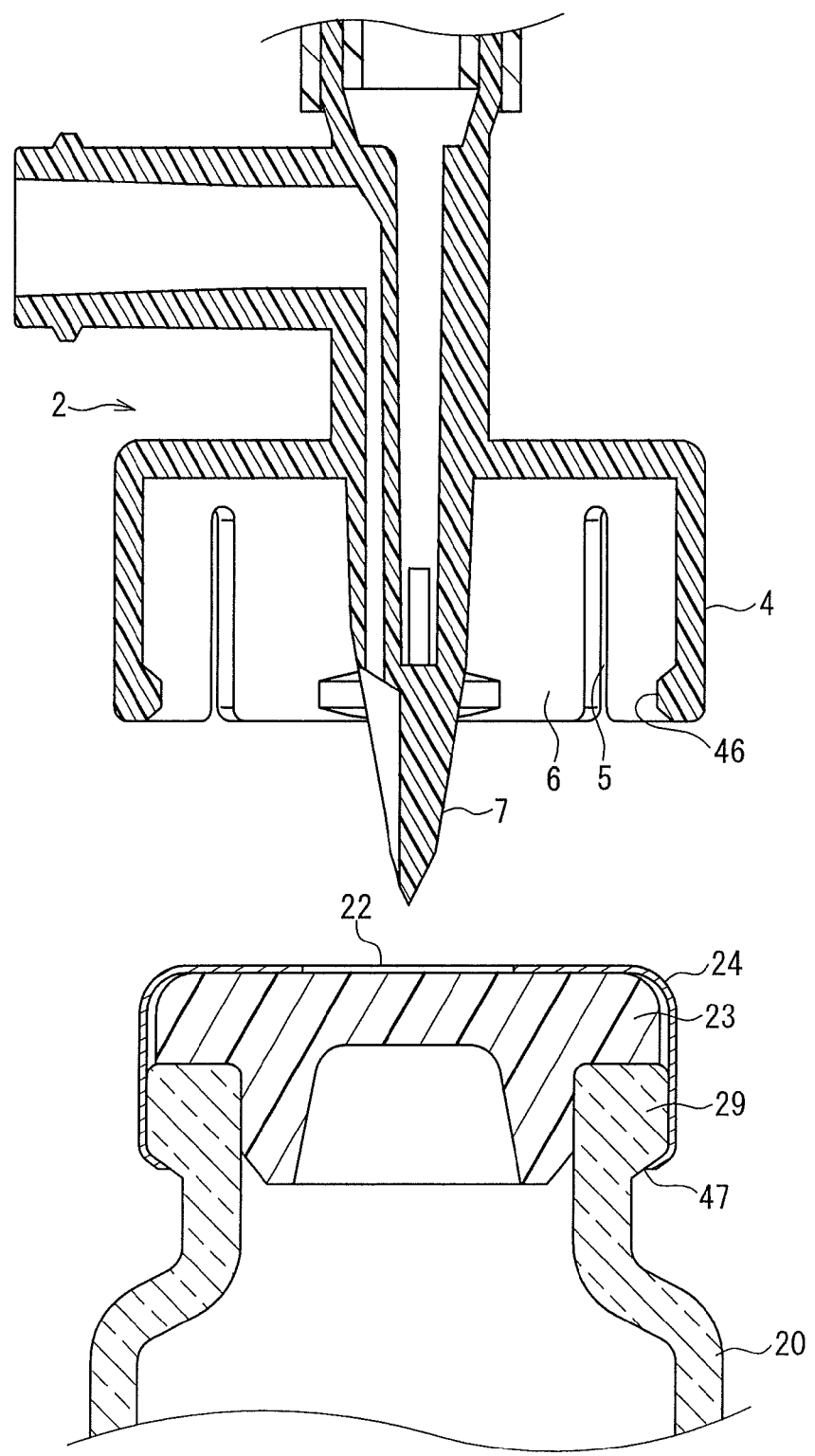
FIG. 9 is a cross-sectional view showing a state before a second connecting portion 4 according to Embodiment 1 of the present invention is connected to the vial 20.

Next, a structure for connecting the second connecting portion 4 to the vial 20 will be described with reference to FIGS. 9 and 10. FIG. 9 is a cross-sectional view showing a state before the second connecting portion 4 is connected to the vial 20. The mouth portion 29 of the vial 20 is sealed with the cap 24 via the rubber stopper 23.

An opening 22 is formed in a central portion of the cap 24. Thus, a portion of the rubber stopper 23 is exposed at the position of the opening 22.

A protrusion 46 protruding from an inner circumferential surface of the connecting port 6 is formed in the second connecting portion 4. An expanded-diameter portion 47 is formed in the mouth portion 29 of the vial 20. As will be described later with reference to FIG. 10, the protrusion 46 of the second connecting portion 4 is to be engaged with the expanded-diameter portion 47 of the vial 20.

Figure 10:
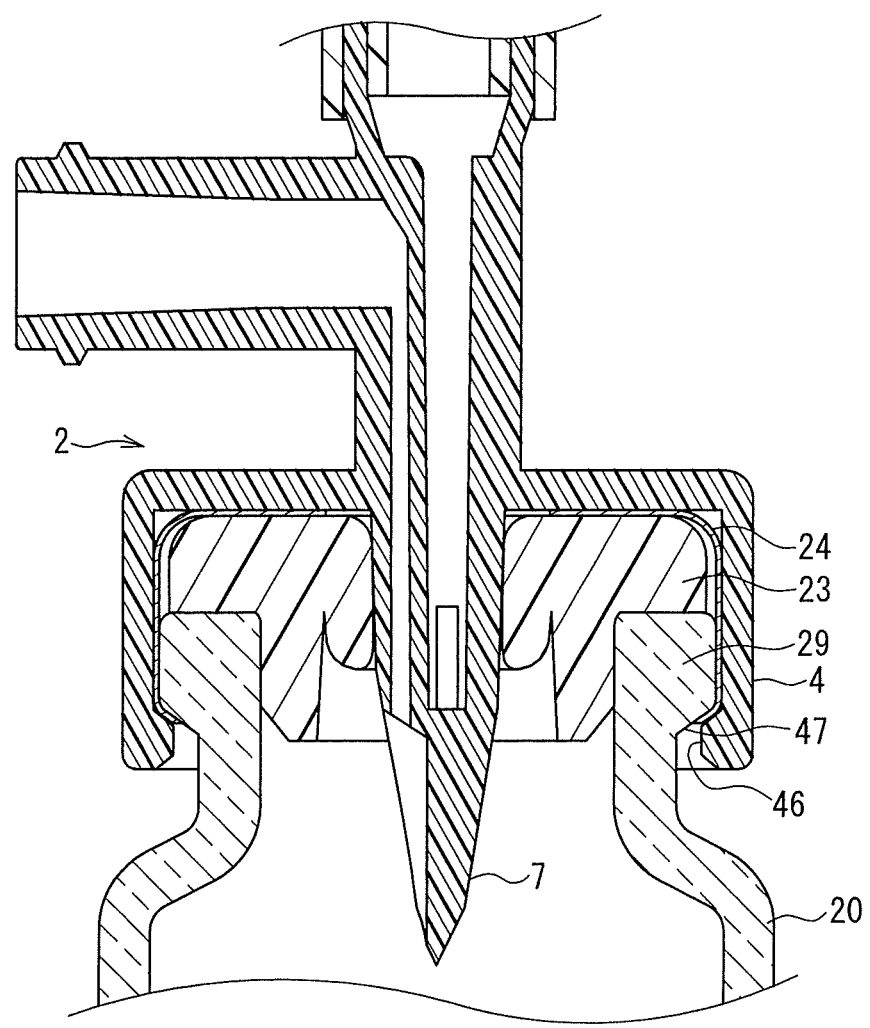
FIG. 10 is a cross-sectional view showing a state in which the second connecting portion 4 according to Embodiment 1 of the present invention has been connected to the vial 20.

FIG. 10 is a cross-sectional view showing a state in which the second connecting portion 4 has been connected to the vial 20. The second connecting portion 4 is engaged with the mouth portion 29 of the vial 20. As shown in FIGS. 3 and 9, slits 5 are formed in a side face of the connecting port 6 and facilitate engagement of the second connecting portion 4 with the vial 20.

In FIG. 10, the rubber stopper 23 of the vial 20 is pierced with the needle-like portion 7 that is integral with the connector main body 2. The protrusion 46 of the second connecting portion 4 is engaged with the expanded-diameter portion 47 of the vial 20, and this prevents the second connecting portion 4 from falling off the vial 20.

Moreover, unlike the first connecting portion 3, the second connecting portion 4 is not provided with a mechanism that facilitates disconnection, such as the lever locks 12. For this reason, if the second connecting portion 4 is engaged firmly with the vial 20, the second connecting portion 4 can be prevented from readily falling off the vial 20. Thus, leakage of the drug solution due to easy detachment of the vial 20 can be prevented.

Moreover, after the first connecting portion 3 has been detached from the drug solution bag 10, the upright tubular portion 25 is covered with the shield 26 as shown in FIG. 7. Therefore, leakage of the drug solution from the upright tubular portion 25 is prevented even after detachment of the first connecting portion 3 from the drug solution bag 10.

Thus, if the vial 20 is disposed of in a state in which the first connecting portion 3 has been detached from the drug solution bag 10 and the second connecting portion 4 and the vial 20 remain in the connected state, leakage of the drug in the vial 20 is prevented.

The drug leakage preventing structure as described above is particularly effective in the case where the drug in the vial 20 is a highly toxic drug such as an anticancer agent.

It should be noted that the second connecting portion 4 of the present embodiment is merely an example, and various types of connecting systems can be employed. For example, although the second connecting portion 4 in FIG. 10 is configured so as to engage the mouth portion 29 of the vial 20, it may be configured so as to engage a body portion thereof.

Moreover, the second connecting portion 4 is formed integrally with the connector main body 2. However, the second connecting portion 4 may be configured as a component separate from the connector main body 2 as long as a structure that prevents the second connecting portion 4 from readily falling off the connector main body 2 can be achieved.

Moreover, a configuration in which the rubber stopper 23 in the mouth portion 29 of the vial 20 is pierced with the needle-like portion 7 has been described as an example. However, there is no limitation to this configuration, and any configuration can be employed as long as a portion of the vial 20 is pierced with the needle-like portion 7. For example, a configuration in which the vial 20 is entirely formed of a soft material and this soft material is pierced with the needle-like portion 7 may be employed.

Embodiment 2

In Embodiment 1, an example in which the syringe 30 is used to draw air from vial 20 and inject air into the vial 20 has been described. In Embodiment 2, the syringe is replaced with a dropper. The present embodiment has the same configuration as Embodiment 1 except that the syringe is replaced with the dropper. Thus, descriptions of the portions having the same configuration as those of Embodiment 1 are omitted.

Figure 11:
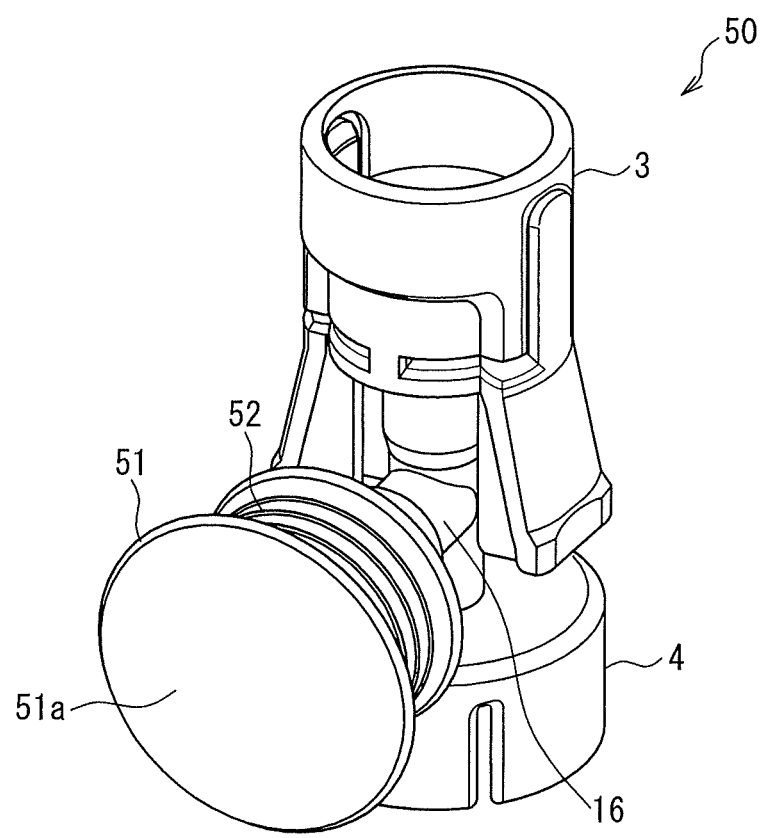
FIG. 11 is a perspective view of a connector 50 according to Embodiment 2 of the present invention.

FIG. 11 shows a perspective view of a connector 50 according to Embodiment 2. A dropper 51 is connected to the horizontal tubular portion 16. The dropper 51 is a dropper with bellows, and a bellows portion 52 can expand and contract in an axial direction of the horizontal tubular portion 16.

Figure 12:
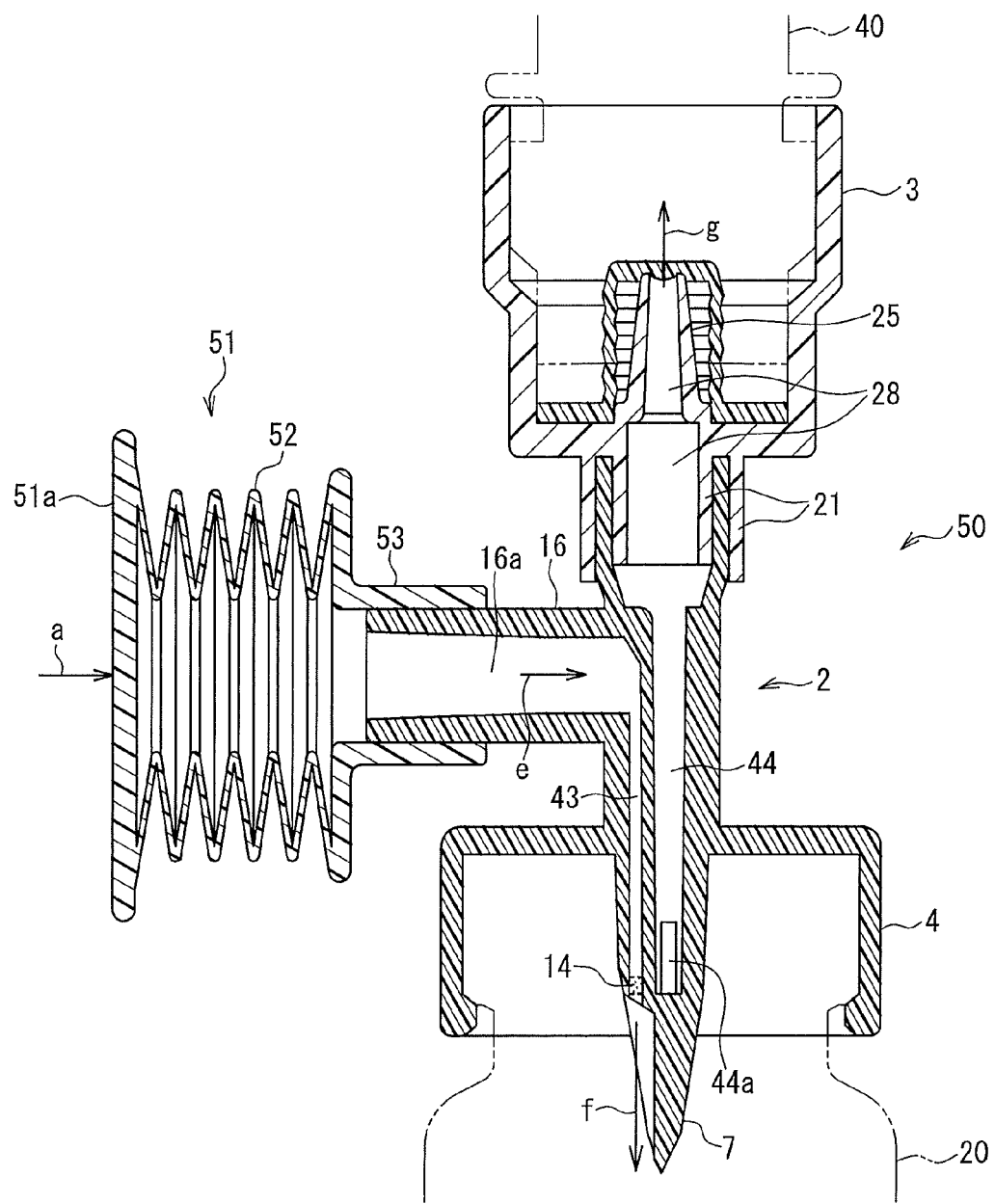
FIG. 12 is a vertical cross-sectional view of the connector 50 shown in FIG. 11.

FIG. 12 shows a vertical cross-sectional view of the connector 50 shown in FIG. 11. An inner circumferential surface of a tubular portion 53 that is integral with the dropper 51 is fitted to an outer circumferential surface of the horizontal tubular portion 16 to connect the dropper 51 to the connector main body 2.

When an end face 51a of the dropper 51 is pressed in the direction of arrow "a", the bellows portion 52 is compressed, and air in the dropper 51 is expelled into the inner space 16a of the horizontal tubular portion 16. The air that has reached the inner space 16a flows in the direction of arrow "e" and passes through the first flow channel 43 and the hydrophobic filter 14 to be injected into the vial 20 as indicated by arrow "f".

At this time, air in the vial 20 passes through the opening 44a, the second flow channel 44, the inner spaces 28 of the upright tubular portion 25 and the connecting tubular portion 21 to reach the connecting port 40 as indicated by arrow "g", and is injected into the drug solution bag 10. When the pressing force on the end face 51a of the dropper 51 is released, the bellows portion 52 is restored. The restoration of the bellows portion 52 causes air in the vial 20 to flow into the bellows portion 52.

In this case, the pressure in the vial 20 is reduced, and thus, into the vial 20, the solvent in the drug solution bag 10 is injected into the vial 20 through the inner spaces 28 of the upright tubular portion 25 and the connecting tubular portion 21, the second flow channel 44, and the opening 44a.

That is to say, by repeating the operation of pressing against the end face 51a of the dropper 51 and the operation of releasing the pressing force, the solvent in the drug solution bag 10 continues to be injected into the vial 20 with the bellows portion 52 of the dropper 51 repeating expansion and contraction. Once the solvent is injected into the vial 20, the drug in powder form contained in the vial 20 is dissolved in the solvent.

Figure 13:
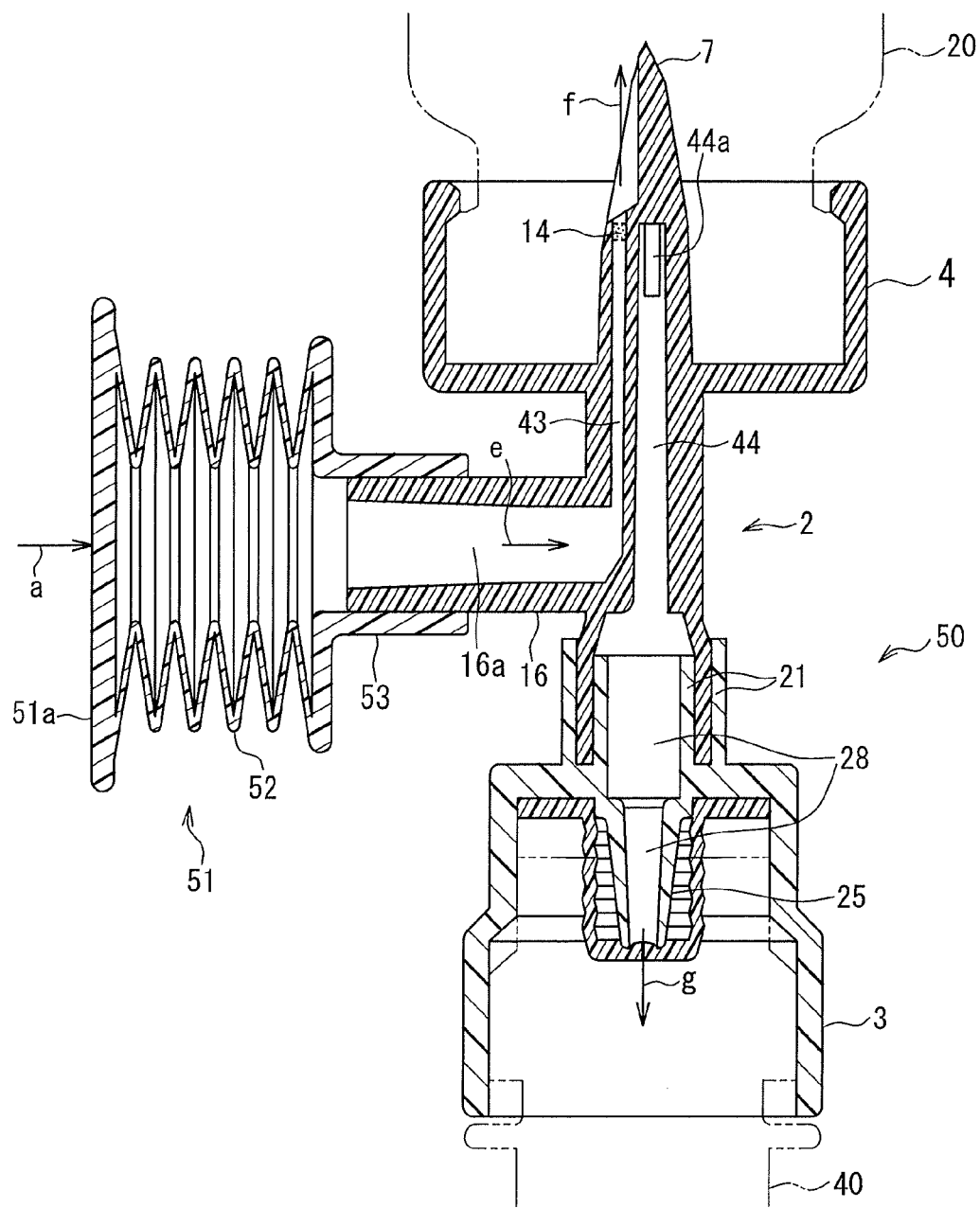
FIG. 13 is a cross-sectional view showing a state in which a drug solution that has been generated within the vial 20 by dissolving a drug in powder form is injected into the drug solution bag, according to Embodiment 2 of the present invention.

FIG. 13 is a cross-sectional view showing a state in which the drug solution that has been generated within the vial 20 by dissolving the drug in powder form is injected into the drug solution bag 10.

In FIG. 13, the vertical relationship between the connecting port 40 of the drug solution bag 10 and the vial 20 is inverted with respect to that shown in FIG. 12. That is to say, in FIG. 12, the vial 20 is positioned on the lower side, whereas in FIG. 13, the vial 20 is positioned on the upper side.

In FIG. 13, when the end face 51a of the dropper 51 is pressed in the direction of arrow "a", the bellows portion 52 is compressed, and air in the dropper 51 is expelled into the inner space 16a of the horizontal tubular portion 16. The air that has reached the inner space 16a flows in the direction of arrow "e" and passes through the first flow channel 43 and the hydrophobic filter 14 to be injected into the vial 20 as indicated by arrow "f". At this time, the drug solution in the vial 20 flows out toward the drug solution bag 10 as indicated by arrow "g", through the opening 44a, the second flow channel 44, and the inner spaces 28 of the upright tubular portion 25 and the connecting tubular portion 21.

When the pressing force on the end face 51a of the dropper 51 is released, the bellows portion 52 is restored. In this case, there is a possibility that the drug solution in the vial 20 may flow into the dropper 51 through the first flow channel 43 and the inner space 16a of the horizontal tubular portion 16. In the present embodiment, in order to prevent such an inflow of the drug solution into the dropper 51, the hydrophobic filter 14 is disposed in the first flow channel 43.

The hydrophobic filter 14 has air permeability and allows air, but not liquid, to pass through. Therefore, it is possible to prevent the drug solution in the vial 20 from flowing into the dropper 51 during restoration of the bellows portion 52 of the dropper 51.

It should be noted that although FIGS. 12 and 13 show an example in which the hydrophobic filter 14 is disposed in the first flow channel 43, the hydrophobic filter 14 can be disposed anywhere in a space from the leading end of the first flow channel 43 to the dropper 51 and may be disposed in the inner space 16a of the horizontal tubular portion 16.

After the bellows portion 52 has been restored, when the end face 51a of the dropper 51 is once again pressed against to compress the bellows portion 52, the drug solution in the vial 20 is injected into the drug solution bag 10 as described above.

That is to say, by repeating the operation of pressing the end face 51a of the dropper 51 and the operation of releasing the pressing force, the drug solution in the vial 20 continues to be injected into the drug solution bag 10 with the bellows portion 52 of the dropper 51 repeating expansion and contraction.

Embodiment 3

Figure 14:
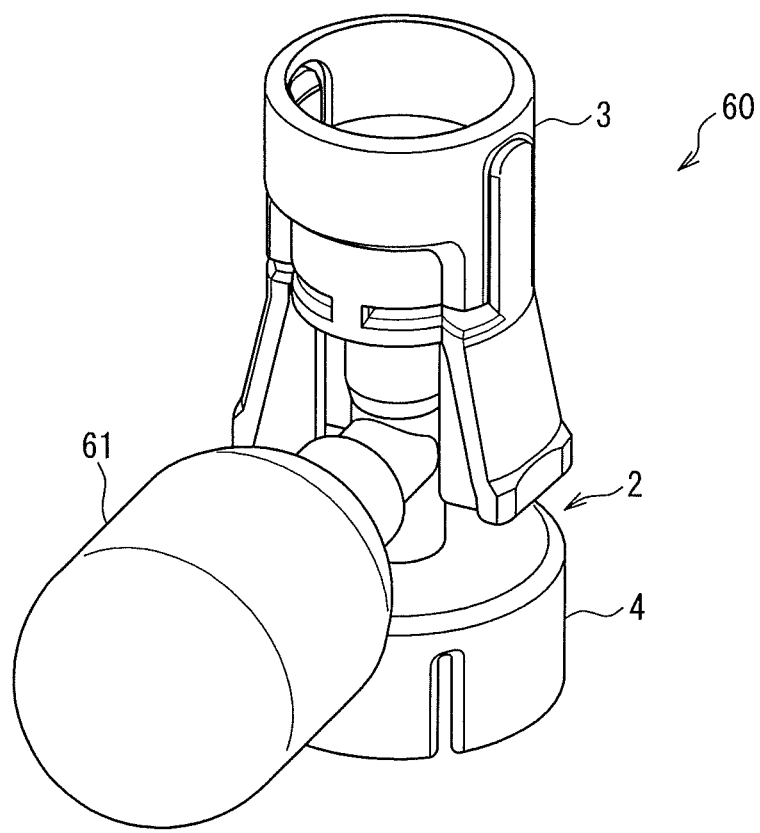
FIG. 14 is a perspective view of a connector 60 according to Embodiment 3 of the present invention.
Figure 15:
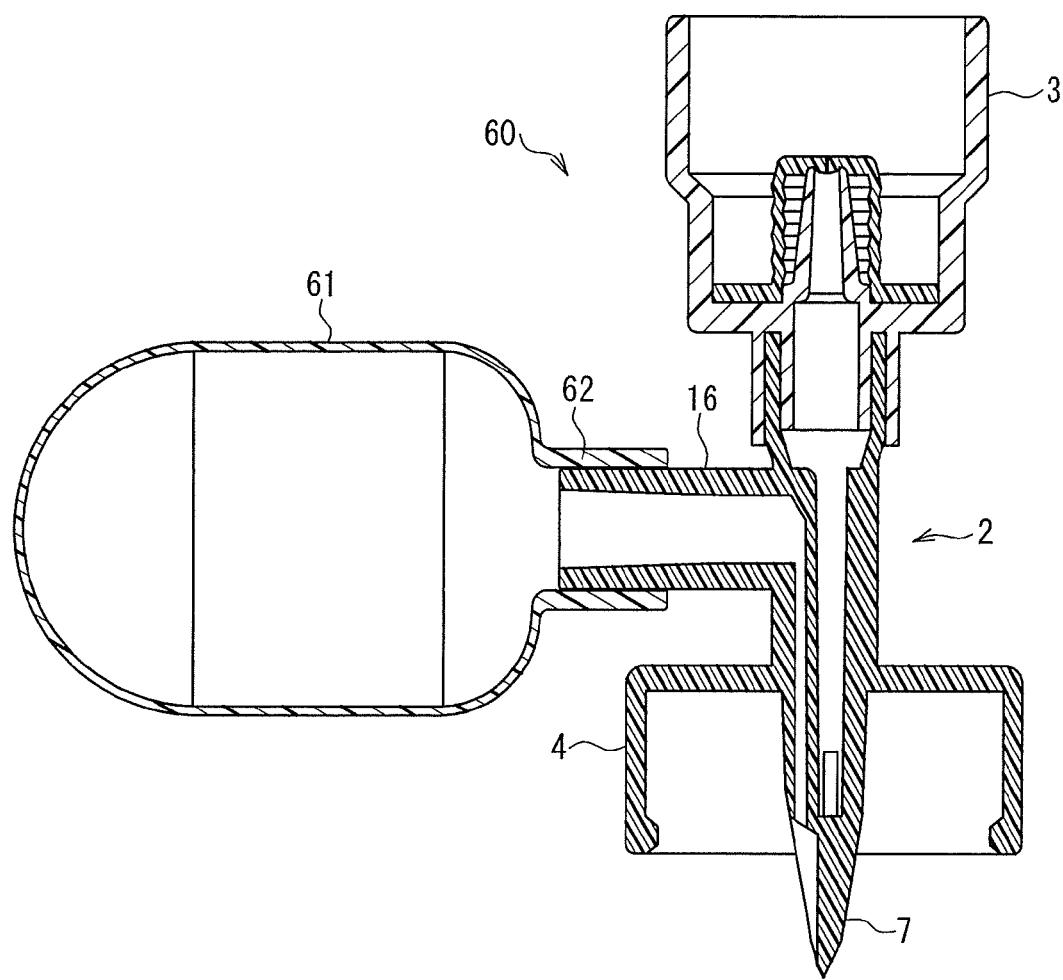
FIG. 15 is a vertical cross-sectional view of the connector 60 shown in FIG. 14.

FIG. 14 shows a perspective view of a connector 60 according to Embodiment 3. FIG. 15 shows a vertical cross-sectional view of the connector 60 shown in FIG. 14. In Embodiment 3, the dropper 51 with bellows of Embodiment 2 is replaced with an ovoid dropper 61. In FIG. 15, an inner circumferential surface of a tubular portion 62 that is integral with the dropper 61 is fitted to the outer circumferential surface of the horizontal tubular portion 16 to connect the dropper 61 to the connector main body 2. Other components are the same as those of Embodiment 2.

The dropper 61 has a cavity inside. By holding and pressing the dropper 61, the dropper 61 is compressed, and thus air can be injected into the vial. When the pressing force is released, the dropper 61 is restored, and thus air is drawn into the dropper 61.

That is to say, by repeating expansion and contraction of the dropper 61, liquid transfer between the vial 20 and the drug solution bag 10 can be achieved by the same effect as that obtained in Embodiment 2 in which the dropper 51 with bellows is used.

Embodiment 4

In Embodiments 1 to 3, an example in which the first connecting portion 3 includes the lever locks 12 that are integral with the connecting port 11 has been described. In Embodiment 4, the first connecting portion has a rotary lock structure.

Figure 16:
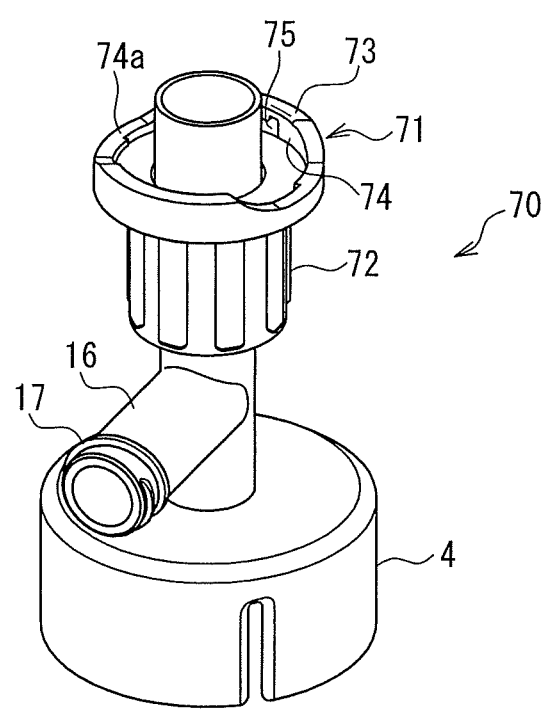
FIG. 16 is a perspective view of a connector 70 according to Embodiment 4 of the present invention.
Figure 17:
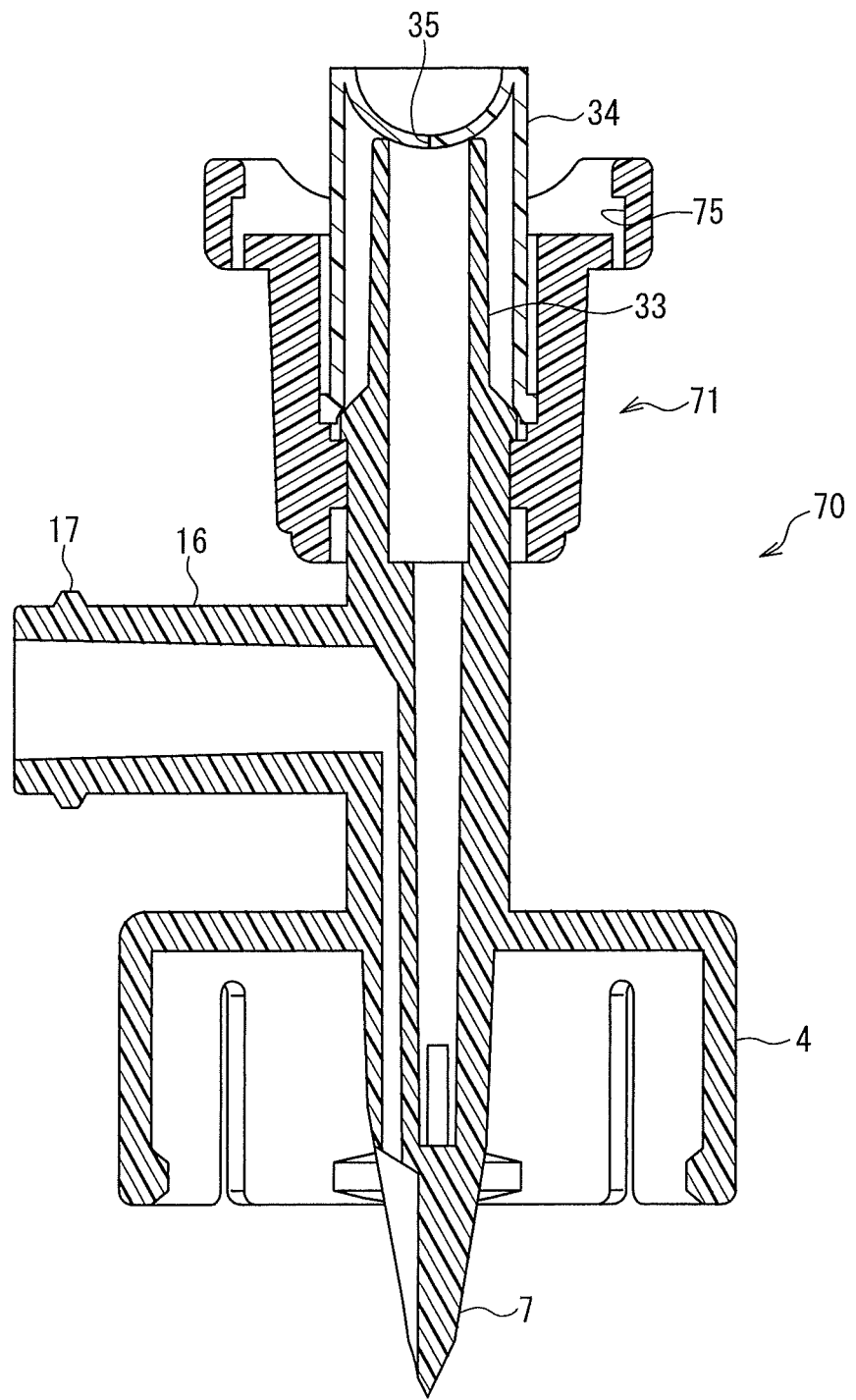
FIG. 17 is a vertical cross-sectional view of the connector 70 shown in FIG. 16.

FIG. 16 shows a perspective view of a connector 70 according to Embodiment 4. FIG. 17 shows a vertical cross-sectional view of the connector 70 shown in FIG. 16. The configuration of the connector 70 corresponds to a configuration in which the first connecting portion 3 including the lever locks 12 of the connector 1 of Embodiment 1 shown in FIG. 3 is replaced with a first connecting portion 71 having a rotary lock structure.

The connector 1 of Embodiment 1 and the connector 70 of the present embodiment have the same configuration except for the first connecting portion 71, even though the other components may be partly different in shape. Therefore, the operating principle of liquid transfer between the first connecting portion 71 side (the drug solution bag 10 side) and the second connecting portion 4 side (the vial 20 side) is also the same as that of Embodiment 1.

In the example shown in FIGS. 16 and 17, the thread 17 is formed on the horizontal tubular portion 16, and so the syringe 30 can be connected to the horizontal tubular portion 16 as is the case with the configuration shown in FIG. 5 of Embodiment 1.

Figure 18:
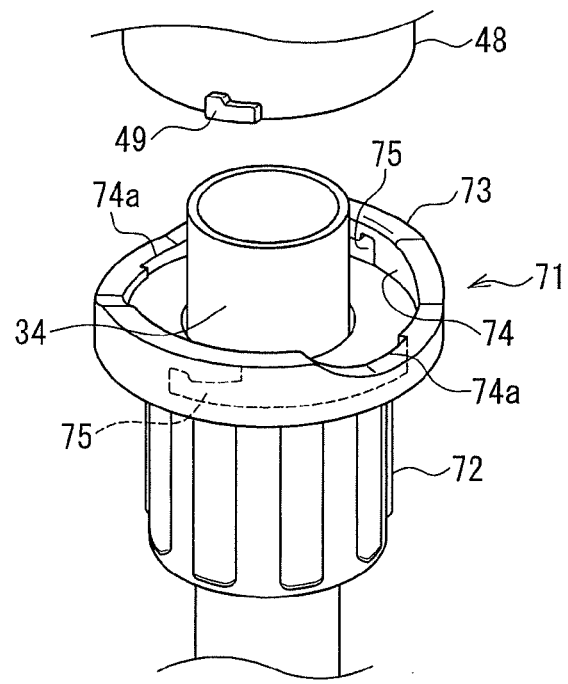
FIG. 18 is a partly enlarged view showing a state before a first connecting portion 71 is connected to the drug solution bag 10 side, according to Embodiment 4 of the present invention.

FIG. 18 is a partly enlarged view showing a state before the first connecting portion 71 is connected to the drug solution bag 10 side. The first connecting portion 71 is integrally provided with a main body 72 and an expanded-diameter portion 73, and a flange 74 is disposed upright in the expanded-diameter portion 73. Notches 74a are formed in the flange 74. Furthermore, recessed grooves 75 are formed in the flange 74. The recessed grooves 75 are grooves that are sunken from an inner circumferential surface of the flange 74. The hollows of the recessed grooves 75 are integral with respective hollows formed by the notches 74a.

A port portion 48 corresponds to the port portion 41 in FIG. 7 of Embodiment 1. Projections 49 are formed on an outer circumferential surface of the port portion 48. The external shape of the projections 49 is set to a shape that is engageable with the recessed grooves 75 of the first connecting portion 71.

During connection of the first connecting portion 71 to the port portion 48, the first connecting portion 71 is brought close to the port portion 48, and the projections 49 of the port portion 48 are put in positions respectively corresponding to the positions of the notches 74a. In this state, when the first connecting portion 71 is rotated around its axis, the projections 49 approach the recessed grooves 75 while the projections 49 remain positioned on the inner circumferential surface side of the flange 74. When the first connecting portion 71 continues to be rotated around its axis, the recessed grooves 75 are brought into engagement with the projections 49, and thus the first connecting portion 71 is connected to the port portion 48.

If the first connecting portion 71 is rotated around its axis in reverse from the above-described direction of rotation, the engagement between the projections 49 and the recessed grooves 75 can be released to detach the first connecting portion 71 from the port portion 48.

Here, in FIG. 17, an upright tubular portion 33 is covered with a shield 34. This configuration is similar to the configuration shown in FIG. 7 in which the upright tubular portion 25 is covered with the shield 26, even though the shape is different. Moreover, although not shown in FIG. 18, a septum that is similar to the septum 42 with the slit 45 shown in FIG. 7 is provided inside the port portion 48.

Thus, in the present embodiment as well, in a state in which the first connecting portion 71 has been connected to the port portion 48, the shield 34 is compressed, so a leading end portion of the upright tubular portion 33 extends outside a slit 35 of the shield 34, and also the leading end portion of the upright tubular portion 33 forces the slit of the septum in the port portion 48 open to bring an inner space of the upright tubular portion 33 into communication with an inner space of the port portion 48, as is the case with the connected state in FIG. 8.

Embodiment 5

Figure 19:
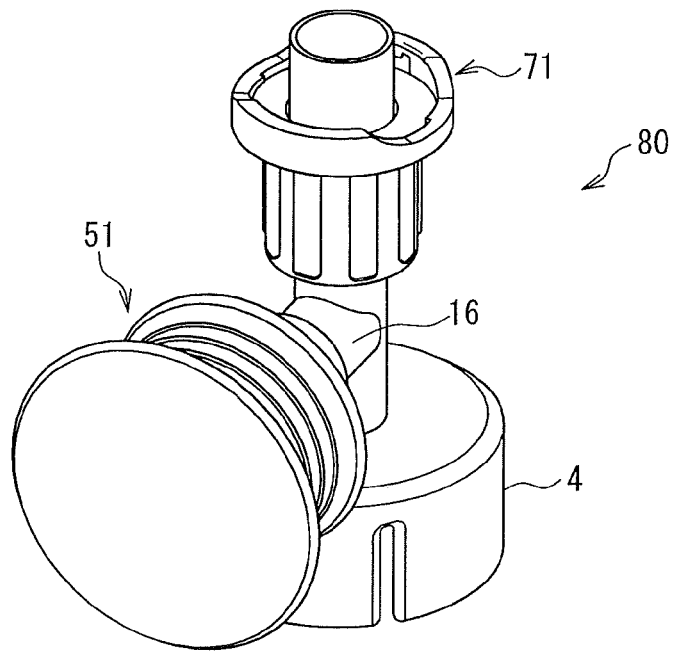
FIG. 19 is a perspective view of a connector 80 according to Embodiment 5 of the present invention.

FIG. 19 shows a perspective view of a connector 80 according to Embodiment 5. While Embodiment 4 shown in FIGS. 16 and 17 has been described using an example in which the syringe 30 is connected to the horizontal tubular portion 16, the connector 80 according to Embodiment 5 is a connector in which the dropper 51 with bellows of Embodiment 2 is connected to the horizontal tubular portion 16. Apart from this, the configuration of the connector 80 according to Embodiment 5 is the same as the configuration of the connector 70 according to Embodiment 4.

With the connector 80 according to the present embodiment, the first connecting portion 71 having the rotary lock structure can be used for connection to the port portion of the drug solution bag 10, as is the case with Embodiment 4. Then, by repeating expansion and contraction of the dropper 51, liquid transfer between the first connecting portion 71 side (the drug solution bag 10 side) and the second connecting portion 4 side (the vial 20 side) can be achieved.

Embodiment 6

Figure 20:
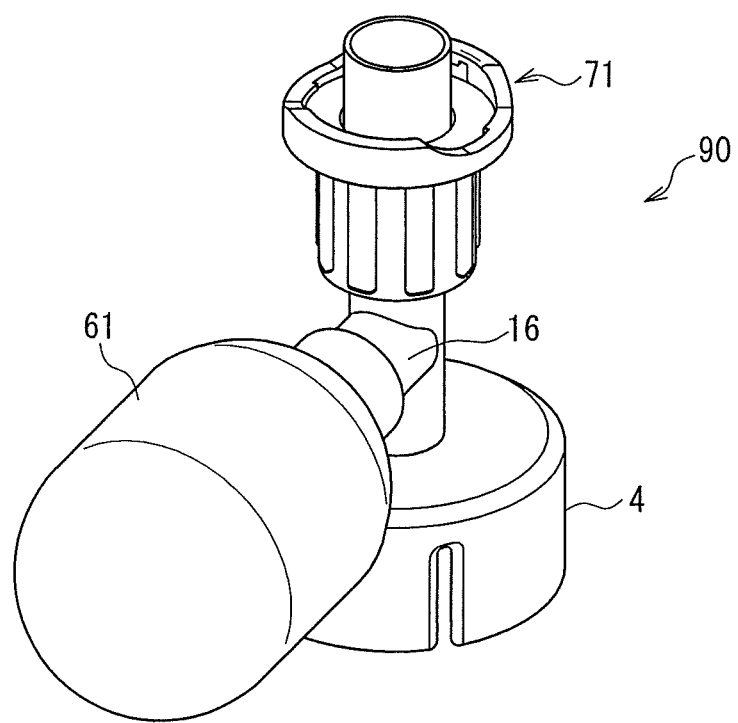
FIG. 20 is a perspective view of a connector 90 according to Embodiment 6 of the present invention.

FIG. 20 shows a perspective view of a connector 90 according to Embodiment 6. While Embodiment 4 shown in FIGS. 16 and 17 has been described using an example in which the syringe 30 is connected to the horizontal tubular portion 16, the connector 90 according to Embodiment 6 is a connecter in which the ovoid dropper 61 of Embodiment 3 is connected to the horizontal tubular portion 16. Apart from this, the configuration of the connector 90 according to Embodiment 6 is the same as the configuration of the connector 70 according to Embodiment 4.

With the connector 90 according to this embodiment, the first connecting portion 71 having the rotary lock structure can be used for connection to the port portion of the drug solution bag 10, as is the case with Embodiment 4. Then, by repeating expansion and contraction of the dropper 61, liquid transfer between the first connecting portion 71 side (the drug solution bag 10 side) and the second connecting portion 4 side (the vial 20 side) can be achieved.

It should noted that in Embodiments 2, 3, 5, and 6, the inner circumferential surface of the tubular portion 53 or 62 that is integral with the dropper 51 or 61 is fitted to the outer circumferential surface of the horizontal tubular portion 16 to connect the dropper 51 or 61 to the connector main body 2. However, this connecting structure may be replaced with other connecting structures. For example, a structure in which a thread formed on the horizontal tubular portion 16 and a thread formed in the tubular portion 53 or 62 are screwed to each other may be employed. Moreover, an adhesive may be used in a connecting portion between the dropper 51 or 61 and the horizontal tubular portion 16 to fix them firmly to each other.

Embodiment 7

Hereinafter, Embodiment 7 of the present invention will be described with reference to the drawings. Embodiment 7 is different from Embodiment 1 in that a flow channel switching mechanism is provided. The portions having the same configuration as those of Embodiment 1 are denoted by the same reference numerals. For convenience of description, these portions denoted by the same reference numerals also will be described again.

Figure 21:
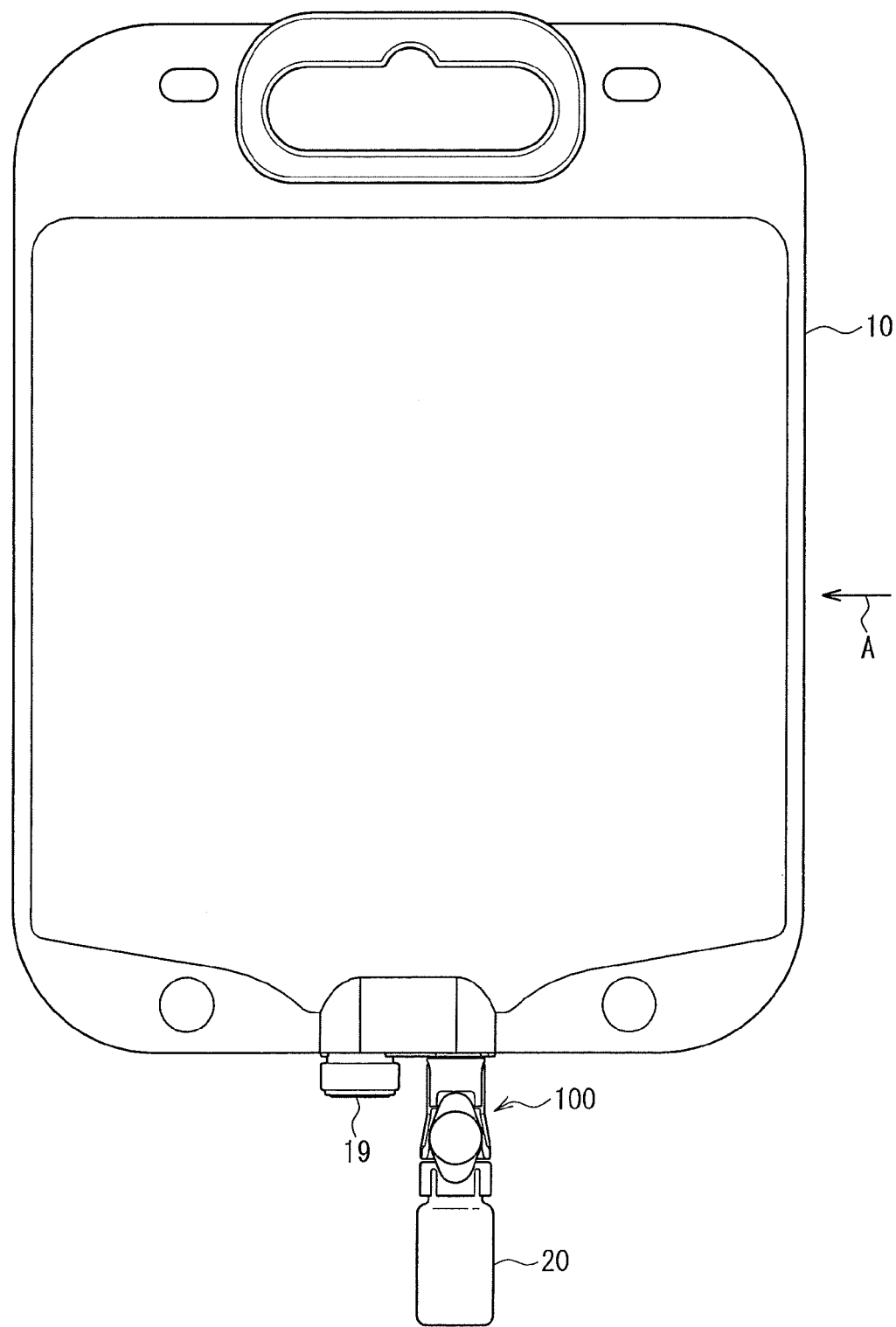
FIG. 21 is a diagram showing an example of use of a connector 100 according to Embodiment 7 of the present invention.

FIG. 21 is a diagram showing an example of use of a connector 100 according to Embodiment 7 of the present invention. In the example shown in this diagram, a drug solution bag 10 and a vial 20 are connected to each other via the connector 100. The drug solution bag 10 is formed by shaping a soft resin sheet into a pouch-like shape. The drug solution bag 10 can be formed by, for example, superposing two resin sheets over each other and joining their peripheral edge portions together by heat welding or the like. The vial 20 is a container containing a drug and is, for example, a glass bottle whose opening is sealed with a rubber stopper and a cap.

Figure 22:
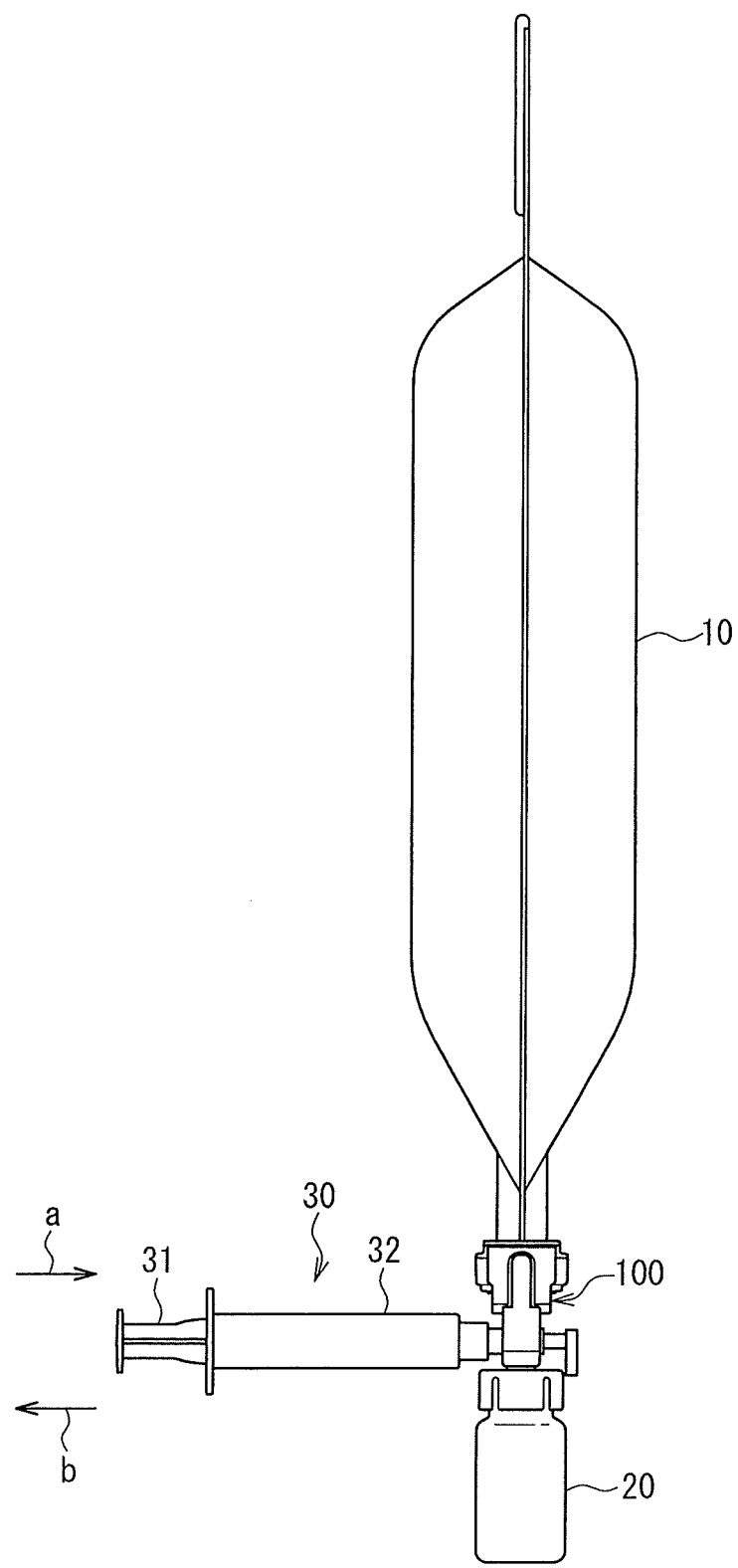
FIG. 22 is a diagram showing the example in FIG. 21 as seen from the direction of arrow A.

FIG. 22 shows the example in FIG. 21 as seen from the direction of arrow A. A syringe 30 is attached to the connector 100. The syringe 30 includes a hollow cylindrical cylinder 32 and a movable piston 31. Pushing the piston 31 in the direction of arrow "a" can cause a liquid in the cylinder 32 to be ejected from the leading end of the cylinder 32. On the other hand, pulling the piston 31 in the direction of arrow "b" can cause a liquid to be drawn into the cylinder 32.

Figure 23:
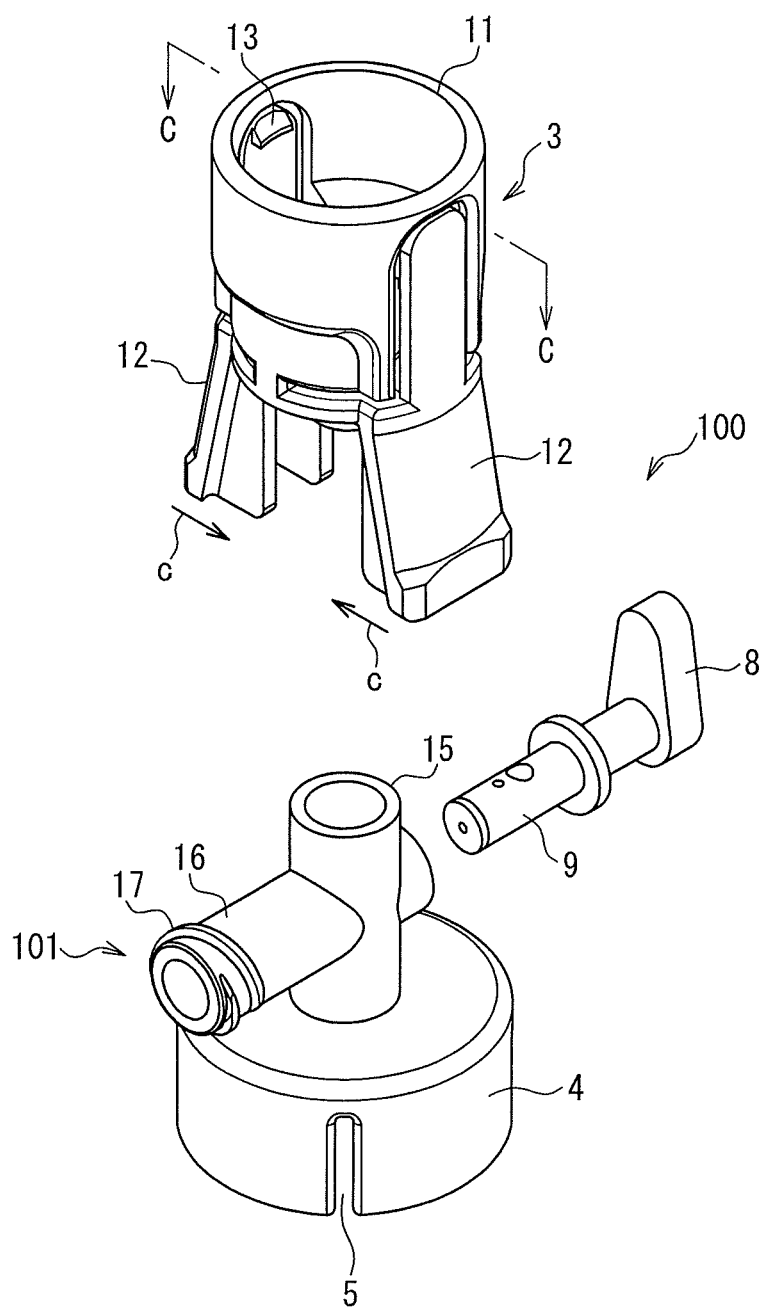
FIG. 23 is an exploded perspective view of the connector 100 according to Embodiment 7 of the present invention.

FIG. 23 is an exploded perspective view of the connector 100. As shown in FIG. 23, the connector 100 can be disassembled into a connector main body 101, a first connecting portion 3, and a stopcock 9. The connector main body 101 is integral with a second connecting portion 4.

It should be noted that in the following description, the portion denoted by reference numeral 101 in FIG. 23 is referred to as the connector main body 101. However, this is for the sake of convenience, and the connector main body 101 and the first connecting portion 3 connected thereto collectively may be regarded as the connector main body 101.

The first connecting portion 3 is integrally provided with a hollow cylindrical connecting port 11 and lever locks 12. The first connecting portion 3 is a connector for connecting the connector 100 to the drug solution bag 10 (FIG. 21). During connection to the drug solution bag 10, a hollow cylindrical port portion 41 (FIG. 30) that is fixed to the drug solution bag 10 is inserted into the connecting port 11.

At this time, while lower portions of the lever locks 12 are bent in the direction of arrow "c", claw portions 13 of the lever locks 12 engage an end face 41a (FIGS. 30 and 31) of the port portion 41. Details of the connection of the first connecting portion 3 to the drug solution bag 10 will be described later with reference to FIGS. 30 and 31.

The connector main body 101 includes an axial tubular portion 15 and a horizontal tubular portion 16 intersecting with each other. A thread 17 is formed on the horizontal tubular portion 16 for the purpose of screwing to the syringe 30 (FIG. 22). The cylindrical stopcock 9 is inserted into the horizontal tubular portion 16. When a lever 8 is rotated, the stopcock 9 rotates around an axis of the horizontal tubular portion 16.

The connector 100, in a connected state as shown in FIG. 22, transfers a liquid between the drug solution bag 10 and the vial 20 via the syringe 30. By rotating the stopcock 9 (FIG. 23), it is possible to switch between a setting that allows liquid transfer between the drug solution bag 10 and the syringe 30 and a setting that allows liquid transfer between the vial 20 and the syringe 30. Details of this switching will be described later with reference to FIGS. 26 to 29.

As described above, in FIG. 23, the connector main body 101 is integral with the second connecting portion 4. The second connecting portion 4 is for connecting the connector main body 101 to the vial 20. A hollow cylindrical connecting port 6 (FIG. 24) is formed in the second connecting portion 4. During connection of the second connecting portion 4 to the vial 20, a cap portion of the vial 20 is fitted into the connecting port 6 of the second connecting portion 4. Details of this connection will be described later with reference to FIGS. 32 and 33.

Figure 24:
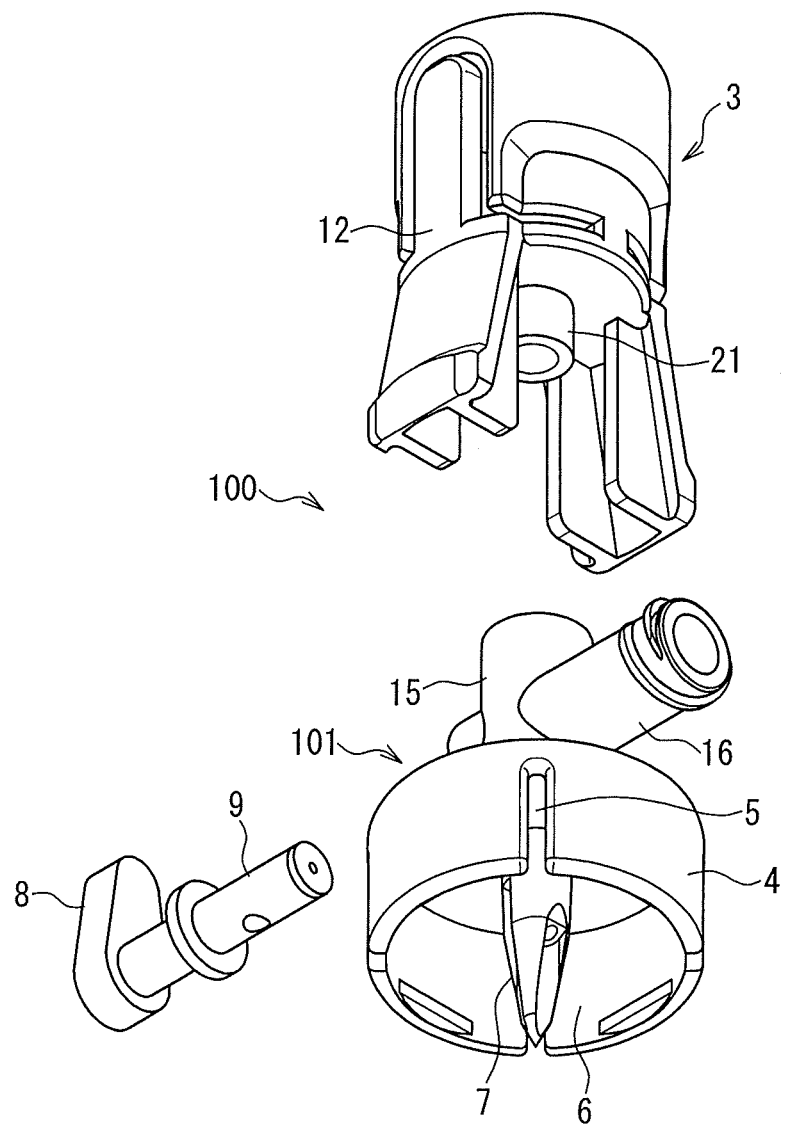
FIG. 24 is an exploded perspective view of the connector 100 in FIG. 23 as seen from a different angle from that of FIG. 23.

FIG. 24 is an exploded perspective view of the connector 100 as seen from a different angle from that of FIG. 23. FIG. 24 shows a back side of the first connecting portion 3 and the connector main body 101. A connecting tubular portion 21 is formed on the back side of the first connecting portion 3. The first connecting portion 3 can be connected to the connector main body 101 by fitting an outer circumferential surface of this connecting tubular portion 21 to an inner circumferential surface (FIG. 23) of the axial tubular portion 15 of the connector main body 101.

A needle-like portion 7 is formed on the back side of the connector main body 101. The needle-like portion 7 has a sharp tip, and a rubber stopper 23 (FIG. 25) of the vial 20 can be pierced with the needle-like portion 7.

Figure 25:
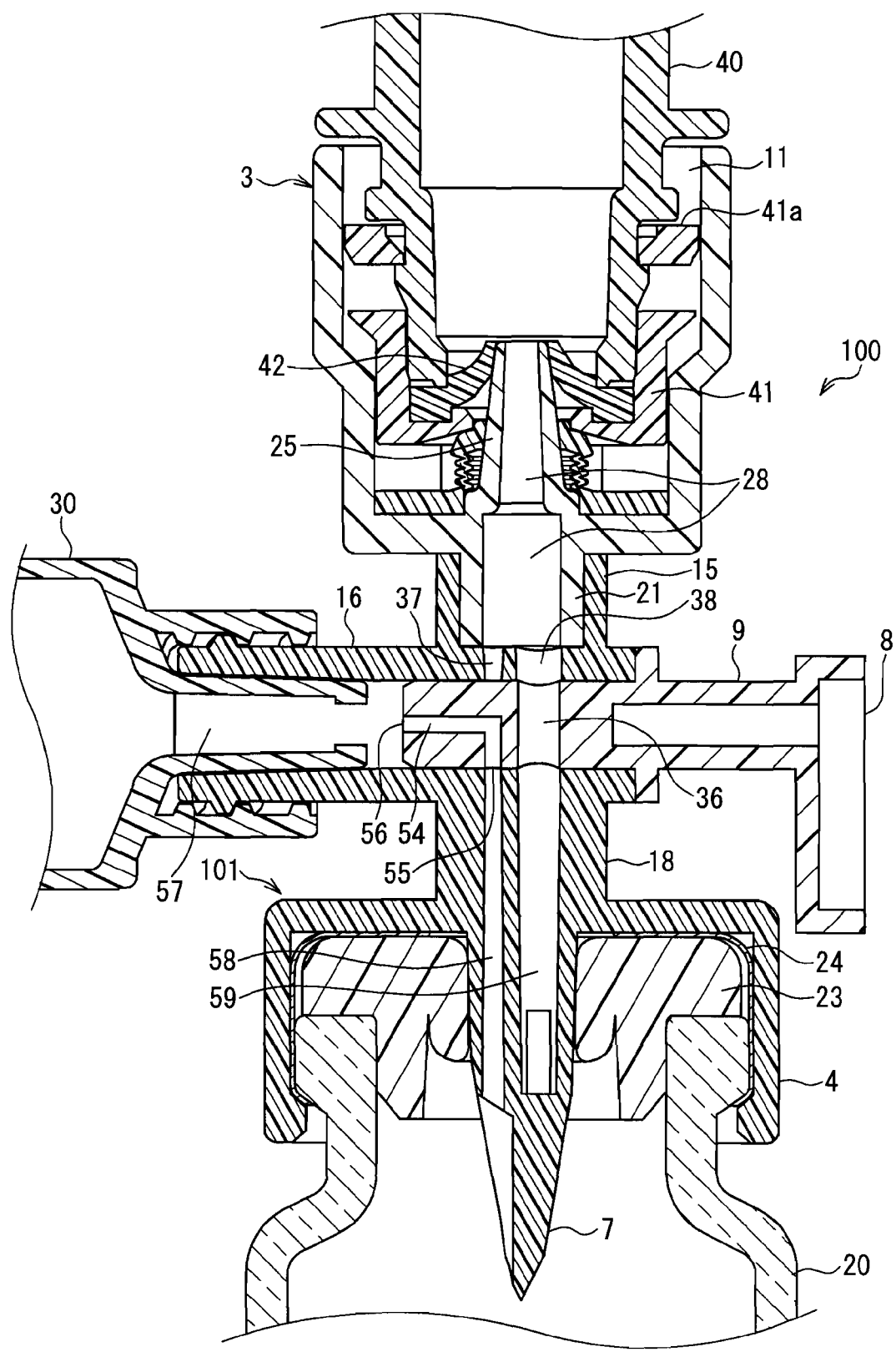
FIG. 25 is a cross-sectional view of the connector according to Embodiment 7 of the present invention.
Figure 30:
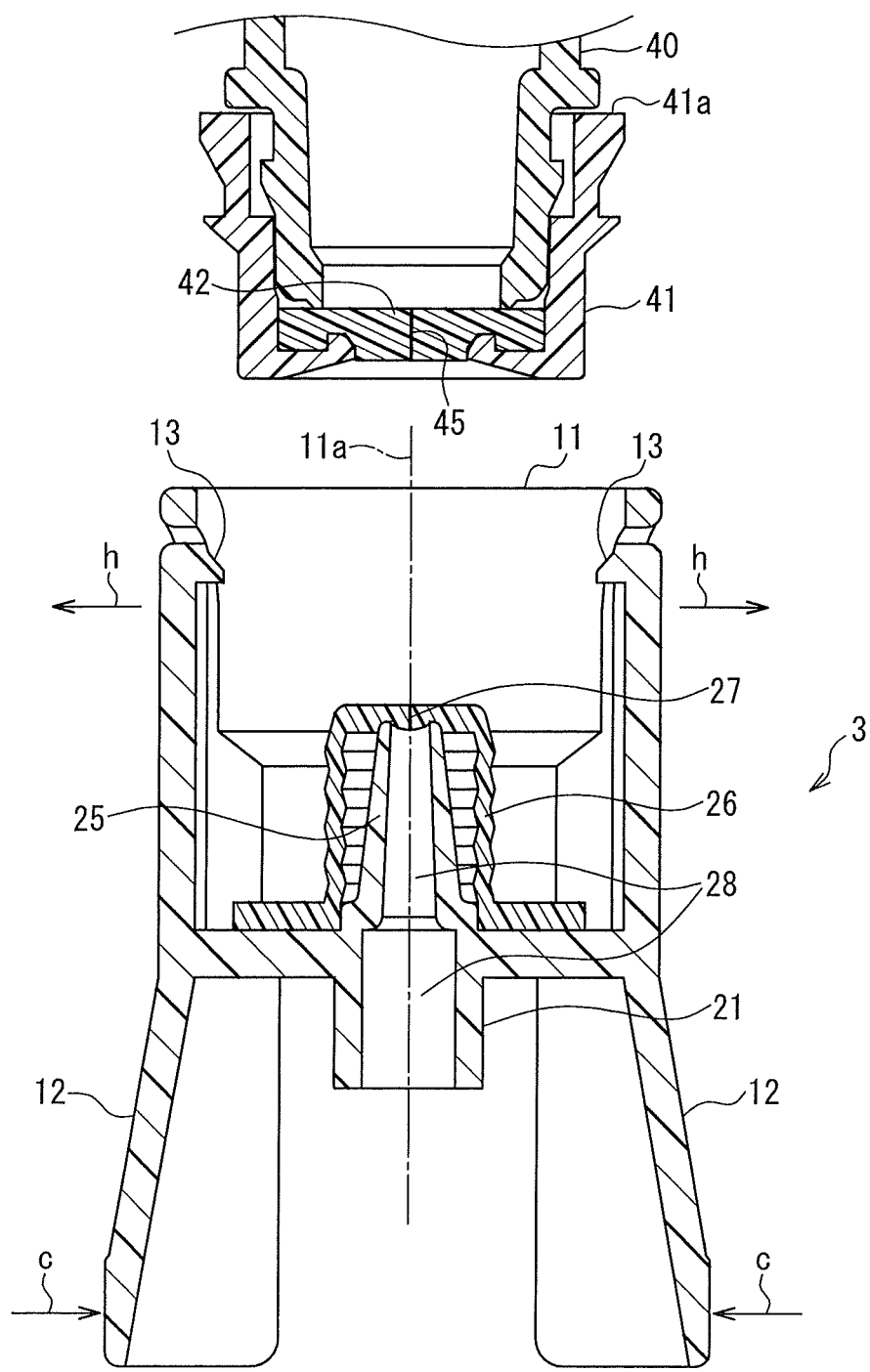
FIG. 30 is a cross-sectional view showing a state before the first connecting portion 3 according to Embodiment 7 of the present invention is connected to the drug solution bag 10.
Figure 31:
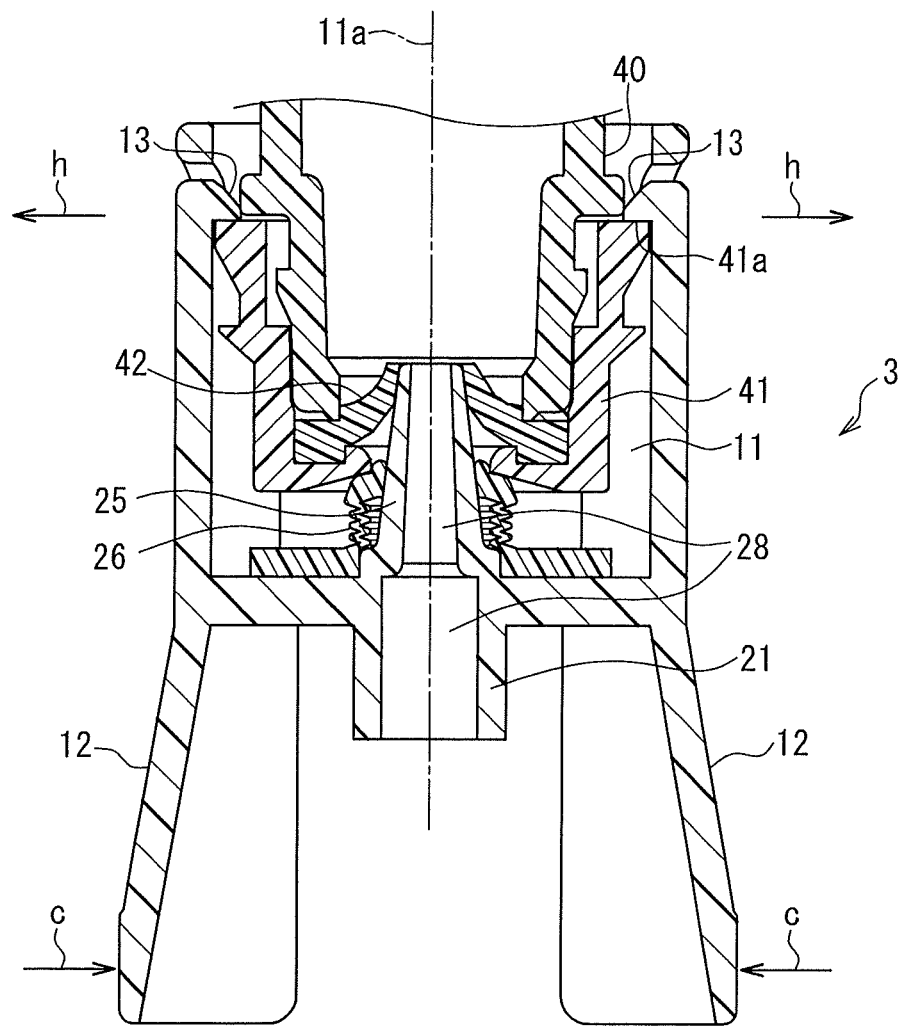
FIG. 31 is a cross-sectional view showing a state in which the first connecting portion 3 according to Embodiment 7 of the present invention has been connected to the port portion 41.

FIG. 25 shows a cross-sectional view of the connector 100. This cross-sectional view corresponds to a vertical cross-sectional view of the connector 100 and its peripheral portions shown in FIG. 22. The port portion 41 is attached to a leading end portion of the connecting port 40 attached to the drug solution bag 10. The port portion 41 is inserted in the connecting port 11 of the first connecting portion 3. Although not shown in this cross-sectional view, the claw portions 13 (FIG. 23) of the lever locks 12 that are integral with the first connecting portion 3 are engaged with the end face 41a of the port portion 41 to connect the first connecting portion 3 to the port portion 41 (FIG. 31). As described above, details of this connection will be described later with reference to FIGS. 30 and 31.

The first connecting portion 3 has an upright tubular portion 25 formed in a central portion of the connecting port 11. A leading end portion of the upright tubular portion 25 pushes up a septum (a partition) 42 attached to the port portion 41. The septum 42 is made of a soft member, and a slit is formed therein. In the state shown in FIG. 25, the leading end portion of the upright tubular portion 25 forces the slit of the septum 42 open by pushing up the septum 42. Thus, an inner space of the connecting port 40 is in communication with inner spaces 28 of the upright tubular portion 25 and the connecting tubular portion 21.

The outer circumferential surface of the connecting tubular portion 21 of the first connecting portion 3 is fitted to the inner circumferential surface of the axial tubular portion 15 of the connector main body 101. Thus, the first connecting portion 3 is connected to the connector main body 101.

The stopcock 9 is inserted in the horizontal tubular portion 16 of the connector main body 101. One end of the horizontal tubular portion 16 is sealed with the stopcock 9, and an open portion 57 is formed at the other end of the horizontal tubular portion 16. An L-shaped flow channel 54 is formed in the stopcock 9, and an opening 56 formed on the open portion 57 side of the horizontal tubular portion 16 is in communication with an opening 55 formed in a side face of the stopcock 9. Furthermore, a penetrating flow channel 36 that passes through the stopcock 9 in a radial direction thereof is formed in the stopcock 9.

It should be noted that in the present embodiment, an example in which the L-shaped flow channel 54 is a flow channel having an L shape has been described. However, all that is required is that the opening 55 and the opening 56 are in communication with each other, and the shape of the flow channel is not limited to an L shape.

A first hole 37 and a second hole 58 are formed in the connector main body 101. These two holes are both holes that bring the inner space of the horizontal tubular portion 16 into communication with an external space of the connector main body 101. The first hole 37 passes through a side wall portion of the horizontal tubular portion 16, and the second hole 58 passes through a base portion 18 and the needle-like portion 7.

Furthermore, a third hole 38 and a fourth hole 59 are formed in the connector main body 101. These two holes are also holes that bring the inner space of the horizontal tubular portion 16 into communication with the external space of the connector main body 101 as is the case with the first hole 37 and the second hole 58. The third hole 38 passes through the side wall portion of the horizontal tubular portion 16, and the fourth hole 59 passes through the base portion 18 and the needle-like portion 7.

When the lever 8 is rotated, the stopcock 9 rotates around the axis of the horizontal tubular portion 16. Due to this rotation, the opening 55 rotationally moves in an outer circumferential direction of the stopcock 9.

In the state shown in FIG. 25, the L-shaped flow channel 54 communicates with the second hole 58. The penetrating flow channel 36 communicates with the third hole 38 and the fourth hole 59. By rotating the lever 8 from this state, the L-shaped flow channel 54 can be set to a state in which it communicates with the first hole 37.

That is to say, by rotating the lever 8, it is possible to switch between a setting that brings the L-shaped flow channel 54 into communication with the second hole 58 and a setting that brings the L-shaped flow channel 54 into communication with the first hole 37. This switching between the settings can be used to transfer a solvent in the drug solution bag 10 into the vial 20 to generate a drug solution by dissolving a drug in powder form contained in the vial 20 in the solvent, and afterward to inject this drug solution into the drug solution bag 10. Details of this will be described later with reference to FIGS. 26 to 29.

The opening of the vial 20 is sealed with the rubber stopper 23 and the cap 24. The rubber stopper 23 is press-fitted in the opening of the vial 20. The cap 24 is formed by, for example, processing a sheet metal, and covers the opening of the vial 20. As shown in FIG. 25, the vial 20 and the connector main body 2 are connected to each other by the second connecting portion 4. Details of this connection will be described later with reference to FIGS. 32 and 33.

Hereinafter, an operating procedure during injection of the drug in the vial 20 into the drug solution bag 10 will be described with reference to FIGS. 26 to 29. In the drawings described below, the connecting port 40, the port portion 41, the syringe 30, and the vial 20 in FIG. 25 are shown simplified in chain double-dashed lines for clarity of illustration.

Figure 26:
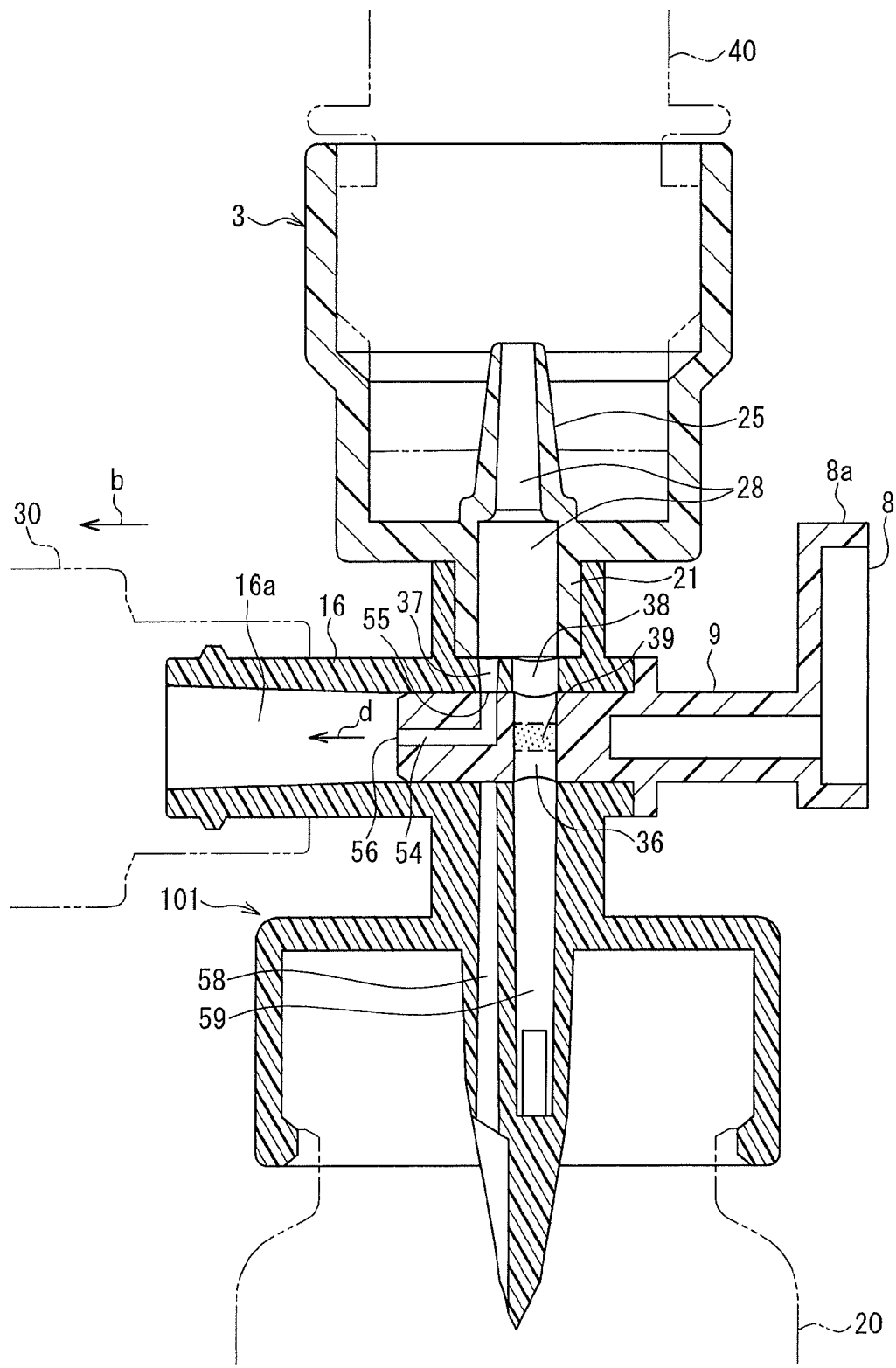
FIG. 26 is a cross-sectional view showing a state in which a solvent in the drug solution bag is drawn into a syringe 30 from a connecting port 40.

FIG. 26 is a cross-sectional view showing a state in which the solvent in the drug solution bag 10 is drawn into the syringe 30 from the connecting port 40. In FIG. 26, the stopcock 9 is in the setting that brings the opening 55 of the L-shaped flow channel 54 into communication with the first hole 37. Accordingly, the solvent in the drug solution bag 10 can flow to the inner space 16a of the horizontal tubular portion 16 through the connecting port 40, the inner spaces 28 of the upright tubular portion 25 and the connecting tubular portion 21, the first hole 37, the L-shaped flow channel 54, and the opening 56.

When the stopcock 9 is in the setting shown in FIG. 26, pulling the piston 31 (FIG. 22) of the syringe 30 in the direction of arrow "b" can cause the solvent in the drug solution bag 10 to be drawn into the inner space 16a of the horizontal tubular portion 16 and further into the syringe 30.

In this case, an amount of the solvent corresponding to the amount by which the piston 31 is pulled is drawn into the syringe 30. Thus, the amount of the solvent to be drawn into the syringe 30 can be adjusted by adjusting the amount by which the piston 31 is pulled while looking at a scale on the cylinder 32. That is to say, a required amount of the solvent can be drawn into the syringe 30 with precision.

In the state shown in FIG. 26, when the pressure in the vial 20 is set to positive pressure, it is possible to prevent the solvent in the drug solution bag 10 from going into the vial 20 through the third hole 38, the penetrating flow channel 36, and the fourth hole 59. To ensure this, a hydrophobic filter can be provided in at least one of the third hole 38, the penetrating flow channel 36, and the fourth hole 59. FIG. 26 shows an example in which a hydrophobic filter 39 is provided in the penetrating flow channel 36.

The hydrophobic filter has air permeability and allows air, but not liquid, to pass through. Therefore, even when the pressure in the vial 20 is not positive, it is possible to prevent the solvent in the drug solution bag 10 from directly flowing into the vial 20.

Figure 27:
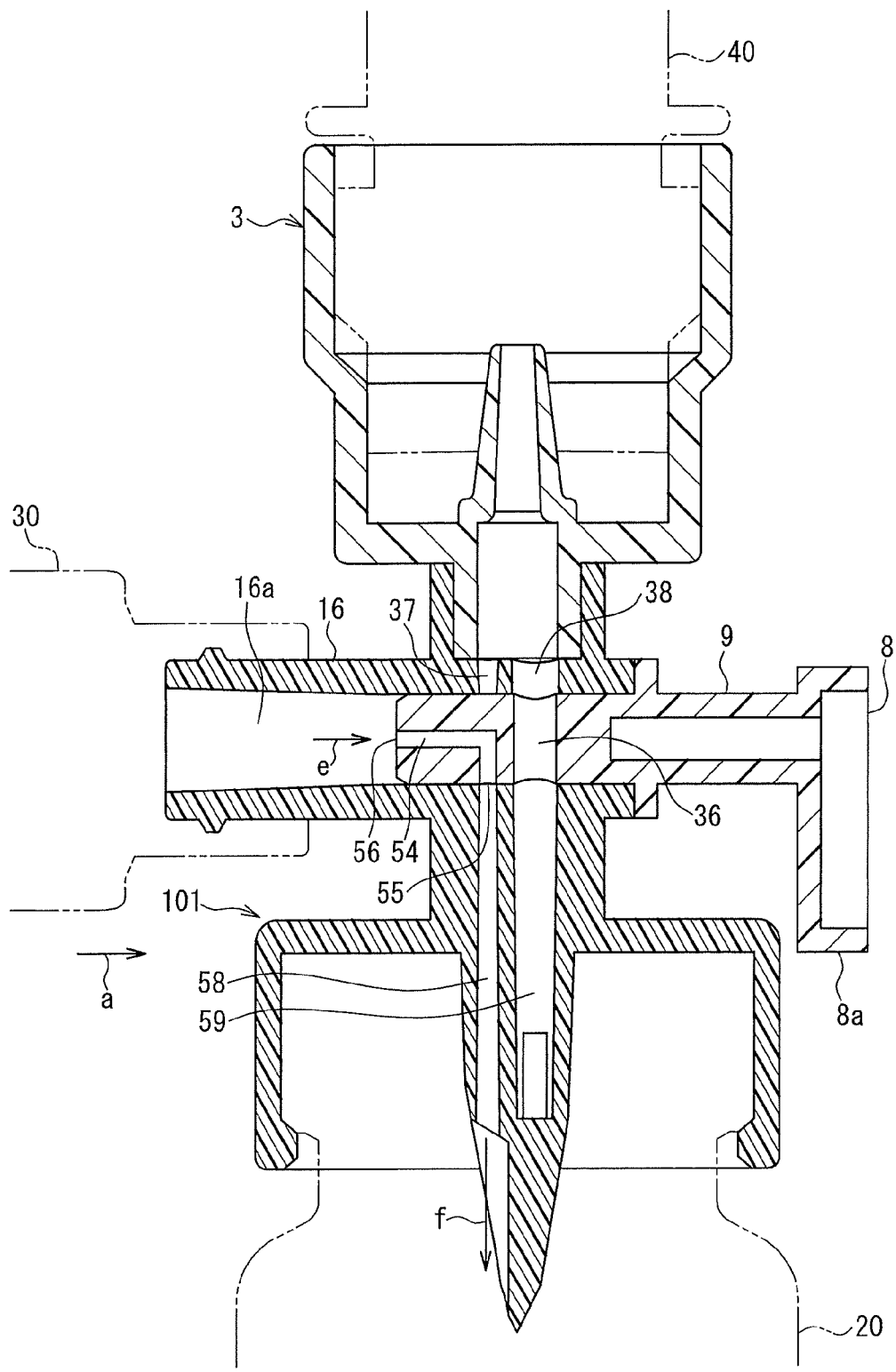
FIG. 27 is a cross-sectional view showing a state in which the solvent that has been drawn into the syringe 30 is injected into the vial 20.

FIG. 27 is a cross-sectional view showing a state in which the solvent that has been drawn into the syringe 30 is injected into the vial 20. The setting of the stopcock 9 shown in FIG.

27 is different from that in FIG. 26. In FIG. 27, the stopcock 9 has been rotated by rotating the lever 8 from the state shown in FIG. 26. In FIG. 26, the opening 55 of the stopcock 9 is positioned on the upper side, whereas in FIG. 27, the opening 55 is positioned on the lower side. That is to say, in FIG. 27, the stopcock 9 is in the setting that brings the L-shaped flow channel 54 into communication with the second hole 58.

In the state shown in FIG. 27, when the piston 31 (FIG. 22) of the syringe 30 is pushed in the direction of arrow "a", the solvent in the syringe 30 is expelled into the inner space 16a of the horizontal tubular portion 16. The solvent that has reached the inner space 16a flows in the direction of arrow "e" and passes through the L-shaped flow channel 54 and the second hole 58 to be injected into the vial 20 as indicated by arrow "f".

In this case, an amount of the solvent corresponding to the amount by which the piston 31 is pushed flows out of the syringe 30. Thus, the amount of the solvent to be caused to flow out of the syringe 30 can be adjusted by adjusting the amount by which the piston 31 is pushed while looking at the scale on the cylinder 32. That is to say, a required amount of the solvent can be injected into the vial 20 with precision.

During injection of the solvent into the vial 20, air in the vial 20 passes up through the fourth hole 59 and flows into the drug solution bag 10 via the connecting port 40. This also applies to the case where a hydrophobic filter is provided in the flow channel from the fourth hole 59 to the third hole 38 as described above. That is to say, the air permeability of the hydrophobic filter allows air in the vial 20 to flow into the drug solution bag 10.

Once the solvent is injected into the vial 20, the drug in powder form contained in the vial 20 is dissolved in the solvent. It is possible to accelerate the dissolution by shaking the vial 20.

Figure 28:
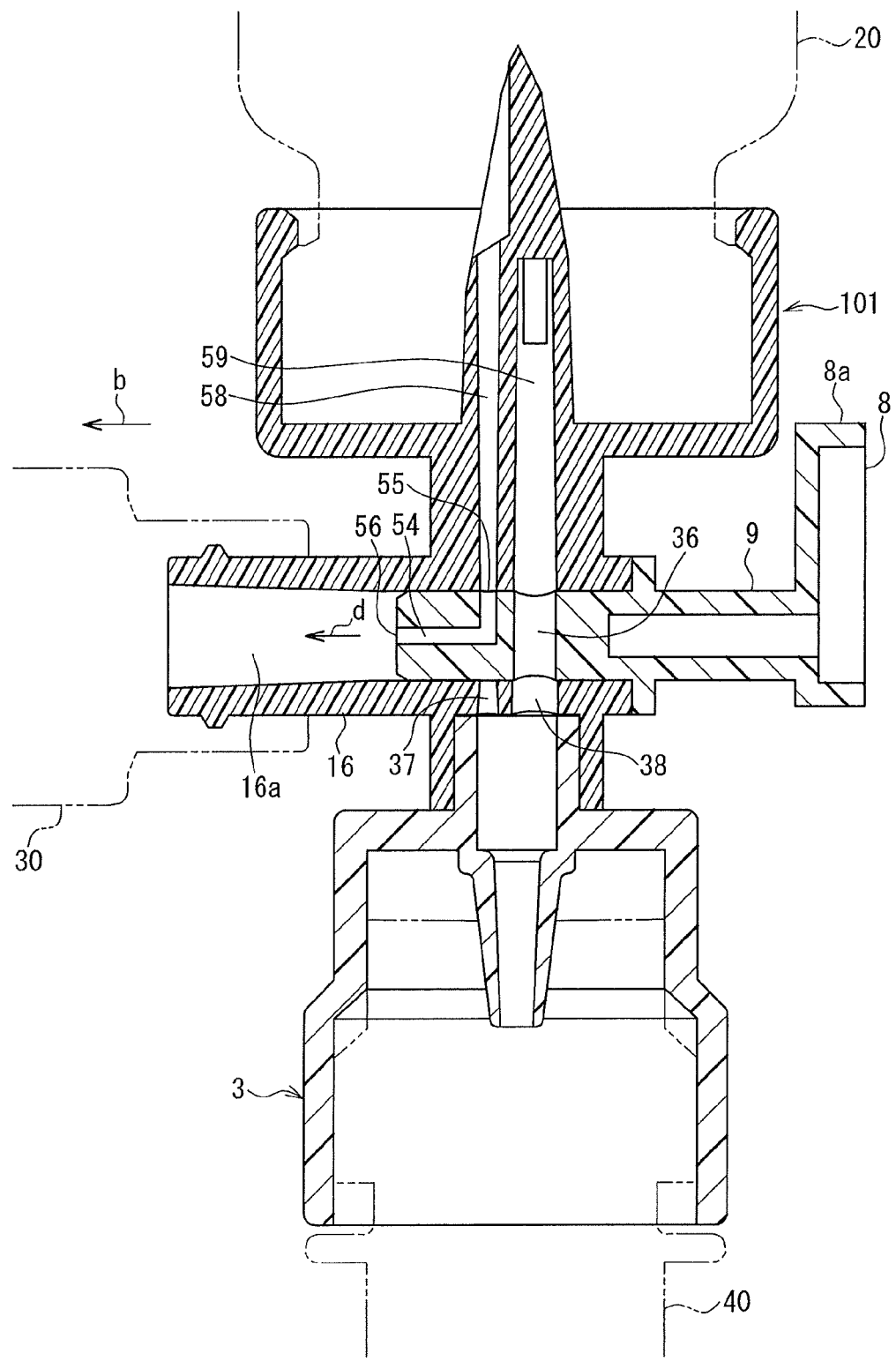
FIG. 28 is a cross-sectional view showing a state in which a drug solution that has been generated within the vial 20 is drawn into the syringe 30.

FIG. 28 is a cross-sectional view showing a state in which the drug solution that has been generated within the vial 20 by dissolving the drug in powder form is drawn into the syringe 30. In FIG. 28, the vertical relationship between the connecting port 40 of the drug solution bag 10 and the vial 20 is inverted with respect to that shown in FIGS. 26 and 27. That is to say, in FIGS. 26 and 27, the vial 20 is positioned on the lower side, whereas in FIG. 28, the vial 20 is positioned on the upper side. In this arrangement, the drug solution in the vial 20 can flow to the inner space 16a of the horizontal tubular portion 16 through the second hole 58 and the L-shaped flow channel 54.

As described above, when a hydrophobic filter is provided in the flow channel from the fourth hole 59 to the third hole 38, it is possible to prevent the drug solution in the vial 20 from directly flowing to the drug solution bag 10 via the connecting port 40 because the drug solution in the vial 20 does not pass through the hydrophobic filter.

When the stopcock 9 is in the setting shown in FIG. 28, pulling the piston 31 (FIG. 22) of the syringe 30 in the direction of arrow "b" can cause the drug solution in the vial 20 to be drawn into the inner space 16a of the horizontal tubular portion 16 and further into the syringe 30.

In this case, an amount of the drug solution corresponding to the amount by which the piston 31 is pulled is drawn into the syringe 30. Therefore, the amount of the drug solution to be drawn into the syringe 30 can be adjusted by adjusting the amount by which the piston 31 is pulled while looking at the scale on the cylinder 32. That is to say, a required amount of the drug solution can be drawn into the syringe 30 with precision.

Figure 29:
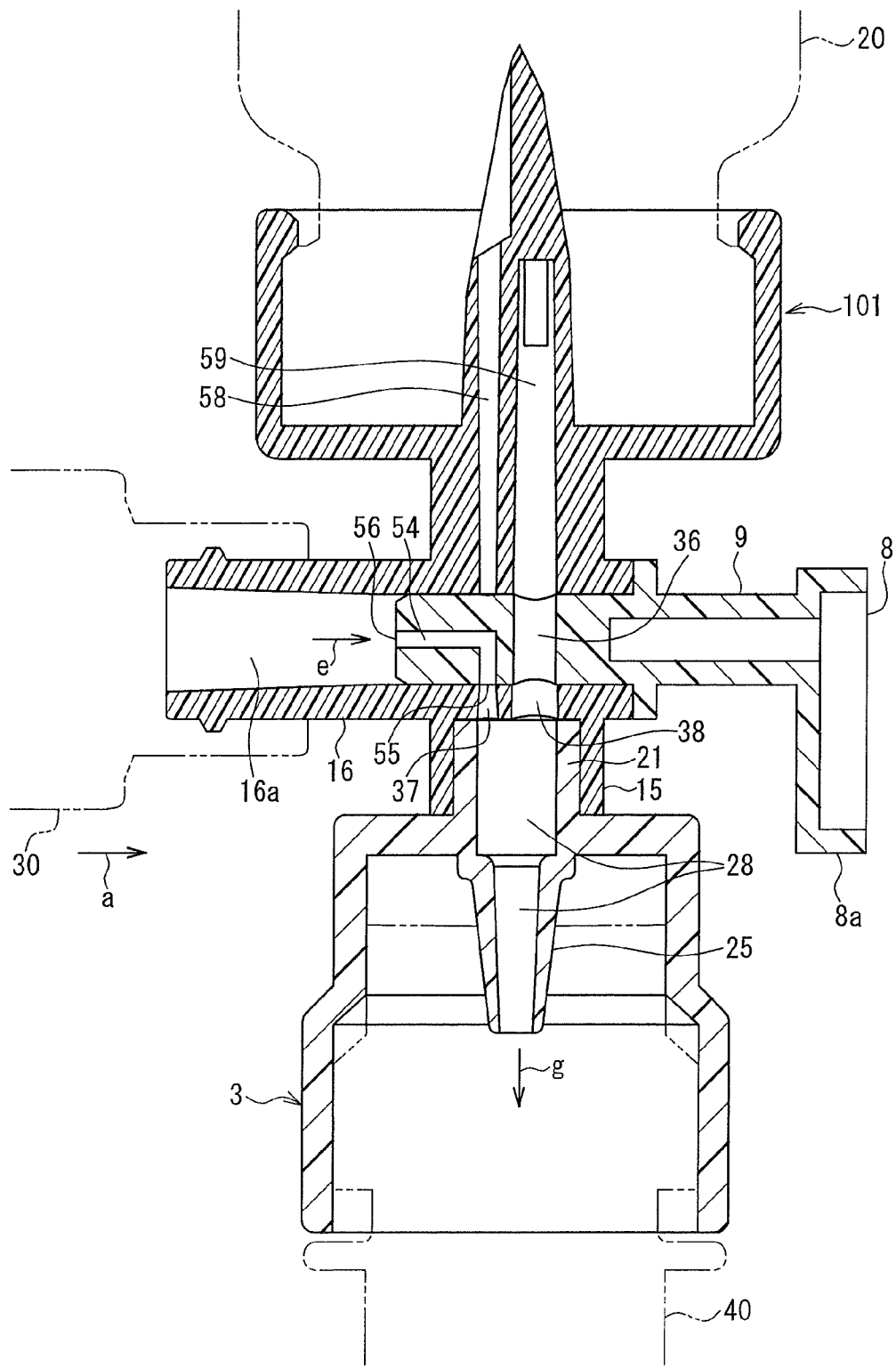
FIG. 29 is a cross-sectional view showing a state in which the drug solution that has been drawn into the syringe 30 is injected into the drug solution bag 10.

FIG. 29 is a cross-sectional view showing a state in which the drug solution that has been drawn into the syringe 30 is injected into the drug solution bag 10. In FIG. 29, the vertical relationship between the bag 10 and the vial 20 is the same as that in the state shown in FIG. 28, and the vial 20 remains positioned on the upper side. In FIG. 29, the setting of the stopcock 9 is different from that in FIG. 28. In FIG. 29, the stopcock 9 has been rotated by rotating the lever 8 from the state shown in FIG. 28. In FIG. 28, the opening 55 of the stopcock 9 is positioned on the upper side, whereas in FIG. 29, the opening 55 is positioned on the lower side. That is to say, in FIG. 29, the stopcock 9 is in the setting that brings the L-shaped flow channel 54 into communication with the first hole 37.

In the state shown in FIG. 29, when the piston 31 (FIG. 22) of the syringe 30 is pushed in the direction of arrow "a", the drug solution in the syringe 30 is expelled into the inner space 16a of the horizontal tubular portion 16. The drug solution that has reached the inner space 16a flows in the direction of arrow "e" and passes through the L-shaped flow channel 54 and the first hole 37 to reach the inner spaces 28 of the connecting tubular portion 21 and the upright tubular portion 25. The drug solution that has reached the inner spaces 28 flows to the connecting port 40 as indicated by arrow "g" and is injected into the drug solution bag 10.

In this case, an amount of the drug solution corresponding to the amount by which the piston 31 is pushed is injected into the drug solution bag 10. Therefore, the amount of the drug solution to be injected into the drug solution bag 10 can be adjusted by adjusting the amount by which the piston 31 is pushed while looking at the scale on the cylinder 32. That is to say, a required amount of the drug solution can be injected into the drug solution bag 10 with precision.

A required amount of the drug solution can be injected into the drug solution bag 10 through the process as described above. The drug solution in the drug solution bag 10 will be administered into the body via a tube with a needle with which a port portion 19 (FIG. 21) is pierced.

In the present embodiment, an example in which the syringe 30 (FIG. 22) and the connector main body 101 are separate components has been described. However, a configuration in which the cylinder portion 32 of the syringe 30 and the connector main body 101 are integral with each other also may be employed. For the cylinder portion 32 and the connector main body 101 to be integral with each other, the cylinder portion 32 may be molded integrally with the horizontal tubular portion 16 (FIG. 23), or the cylinder portion 32 may be fixed to the horizontal tubular portion 16 (FIG. 23) with an adhesive. This configuration eliminates the need for attachment of the syringe 30 and facilitates assembly of the connector 100 prior to operation. Moreover, erroneous detachment of the syringe 30 and resulting opening of the other end of the horizontal tubular portion 16 can be prevented.

Moreover, in the present embodiment, as shown in FIG. 23, the lever 8 extended from the stopcock 9 is formed on the stopcock 9. It is possible to determine the status of the flow channel setting within the connector 100 from the orientation of the lever 8.

Specifically, in FIG. 26, the first hole 37 and the L-shaped flow channel 54 are in communication with each other. A leading end 8a of the lever 8 points to an external space side communicating with the first hole 37, that is, the connecting port 40 side. Thus, it is possible to determine that the connector 100 is in a state in which it enables transfer to/from the drug solution bag 10 side because the leading end 8a of the lever 8 points to the connecting port 40 side.

In FIG. 27, the second hole 58 and the L-shaped flow channel 54 are in communication with each other. The leading end 8*a* of the lever 8 points to an external space side communicating with the second hole 58, that is, the vial 20 side. Thus, it is possible to determine that the connector 100 is in a state in which it enables transfer to/from the vial 20 side because the leading end 8*a* of the lever 8 points to the vial 20 side.

That is to say, with the stopcock 9 equipped with the lever 8 according to the present embodiment, it is possible to determine readily which of the drug solution bag 10 side and the vial 20 side the connector 100 enables transfer to/from by observing the orientation of the leading end 8*a* of the lever 8.

Next, a structure for connecting the first connecting portion 3 to the drug solution bag 10 will be described with reference to FIGS. 30 and 31. FIG. 30 is a cross-sectional view showing a state before the first connecting portion 3 is connected to the drug solution bag 10. As described above, the connecting port 40 is attached to the drug solution bag 10. The port portion 41 is attached to the leading end portion of the connecting port 40. The septum (the partition) 42 in which a slit 45 is formed is attached to the port portion 41.

The first connecting portion 3 shown in FIG. 30 corresponds to a cross-sectional view taken along line CC in FIG. 23. The lever locks 12 are integral with the first connecting portion 3. Bending the lower portions of the lever locks 12 toward the central axis 11*a* of the connecting port 11 (the direction of arrow "c") causes the claw portions 13 of the lever locks 12 to be displaced away from the central axis 11*a* of the connecting port 11 (the direction of arrow "h").

FIG. 31 is a cross-sectional view showing a state in which the first connecting portion 3 has been connected to the port portion 41. The port portion 41 is inserted in the connecting port 11, and also the claw portions 13 of the lever locks 12 are engaged with the end face 41*a* of the port portion 41. During insertion of the port portion 41 into the connecting port 11, in FIG. 30, the lower portions of the lever locks 12 are bent toward the central axis 11*a* of the connecting port 11 (the direction of arrow "c"), and the claw portions 13 of the lever locks 12 are displaced away from the central axis 11*a* of the connecting port 11 (the direction of arrow "h"). Accordingly, once the port portion 41 is inserted into the connecting port 11, the claw portions 13 engage the end face 41*a* of the port portion 41 as shown in FIG. 31.

Here, in FIG. 30, the upright tubular portion 25 that is integral with the first connecting portion 3 is covered with a shield 26 that can open and close by extension and retraction. A slit 27 is formed in the shield 26. When the shield 26 is retracted, a portion where the slit 27 is formed opens (FIG. 31), and when the retracted shield 26 is restored, the portion where the slit 27 is formed closes (FIG. 30).

In the state shown in FIG. 30, the shield 26 covers the upright tubular portion 25, whereas in the state shown in FIG. 31, the shield 26 is retracted, and the upright tubular portion 25 extends outside the shield 26. This is because during insertion of the port portion 41 into the connecting port 11, a lower portion of the port portion 41 presses against the shield 26 such that the shield is pushed down.

A leading end portion of the upright tubular portion 25 extending outside the shield 26 pushes up the septum 42 attached to the port portion 41 and thus forces the slit 45 (FIG. 30) of the septum 42 open. As a result, the inner space of the connecting port 40 is brought into communication with the inner spaces 28 of the upright tubular portion 25 and the connecting tubular portion 21.

Next, after a required amount of the drug solution has been injected into the drug solution bag 10, the first connecting portion 3 that is integral with the vial 20 is to be detached from the port portion 41. During detachment, in FIG. 31, the lower portions of the lever locks 12 can be pressed against toward the central axis 11*a* of the connecting port 11 (the direction of arrow "c"), and the claw portions 13 of the lever locks 12 displaced away from the central axis 11*a* of the connecting port 11 (the direction of arrow "h").

The first connecting portion 3 returns to the state shown in FIG. 30 after being detached from the port portion 41. In the state shown in FIG. 30, the retracted shield 26 has been restored and covers the upright tubular portion 25 again. In this state, leakage of the drug solution in the vial 20 is prevented.

It should be noted that, in FIG. 30, the structure of the upright tubular portion 25 covered with the shield 26 may be provided on the port portion 41 side. In this case, the structure of the port portion 41 in which the opening is covered with the septum 42 that can open and close by extension and retraction will be provided in the first connecting portion 3. According to this configuration, in FIG. 30, although the vertical relationship between the upright tubular portion 25 and the septum 42 is inverted, the fact remains that the inner space of the connecting port 40 is brought into communication with the inner space 28 of the connecting tubular portion 21.

Moreover, the first connecting portion 3 of the present embodiment is merely an example, and various types of connecting systems can be employed. Furthermore, although an example in which the first connecting portion 3 and the connector main body 101 are configured as separate components has been described, a configuration in which the first connecting portion 3 and the connector main body 101 are integrally molded is conceivable depending on the structure of the first connecting portion 3.

Figure 32:
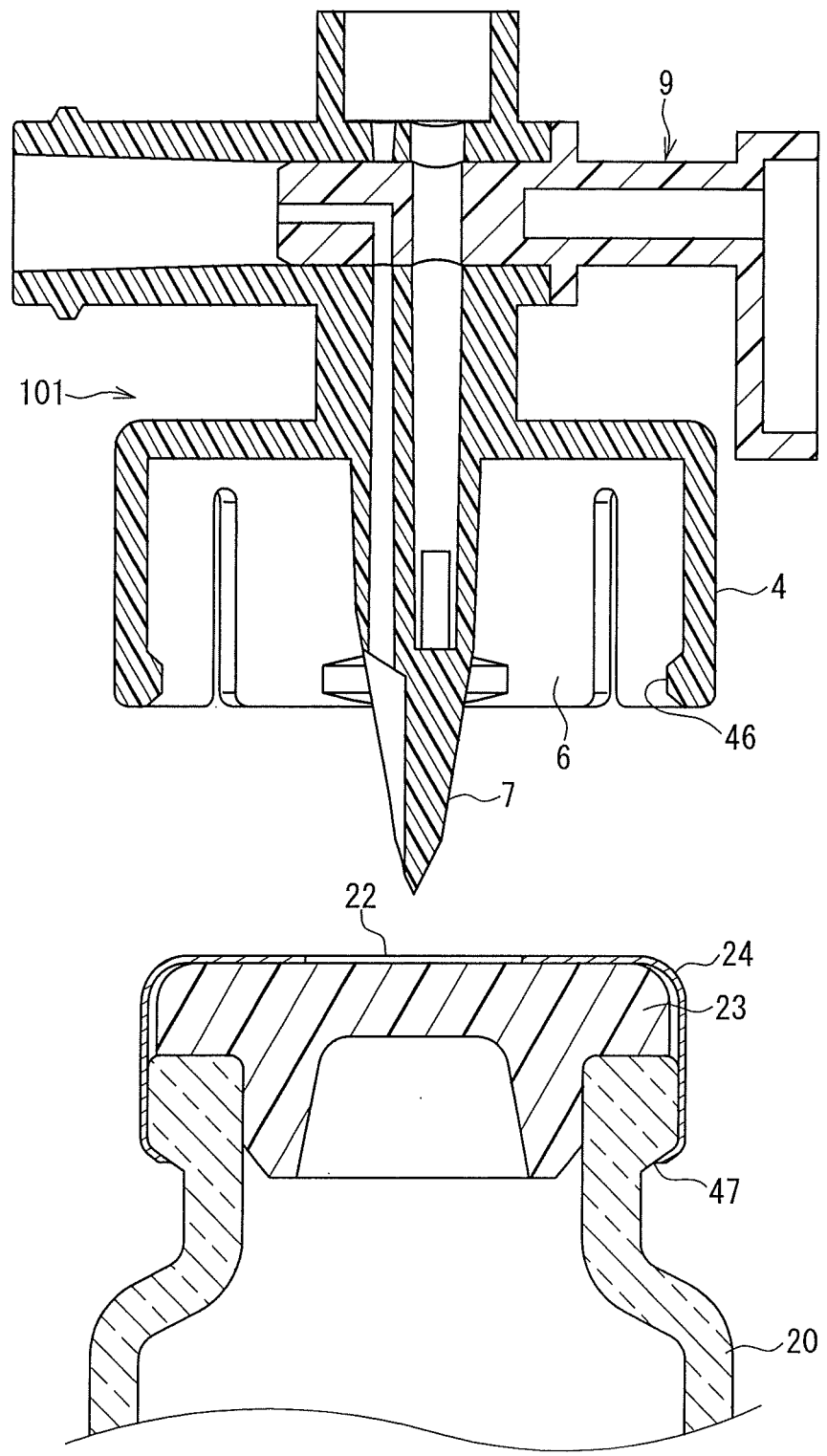
FIG. 32 is a cross-sectional view showing a state before the second connecting portion 4 according to Embodiment 7 of the present invention is connected to the vial 20.

Next, a structure for connecting the second connecting portion 4 to the vial 20 will be described with reference to FIGS. 32 and 33. FIG. 32 is a cross-sectional view showing a state before the second connecting portion 4 is connected to the vial 20. The opening of the vial 20 is sealed with the cap 24 via the rubber stopper 23.

An opening 22 is formed in a central portion of the cap 24. Thus, the rubber stopper 23 is exposed at the position of the opening 22.

A protrusion 46 protruding from an inner circumferential surface of the connecting port 6 is formed in the connecting port 6 of the second connecting portion 4. An expanded-diameter portion 47 is formed on the opening side of the vial 20. As will be described later by means of FIG. 33, the protrusion 46 of the second connecting portion 4 is to be engaged with the expanded-diameter portion 47 of the vial 20.

Figure 33:
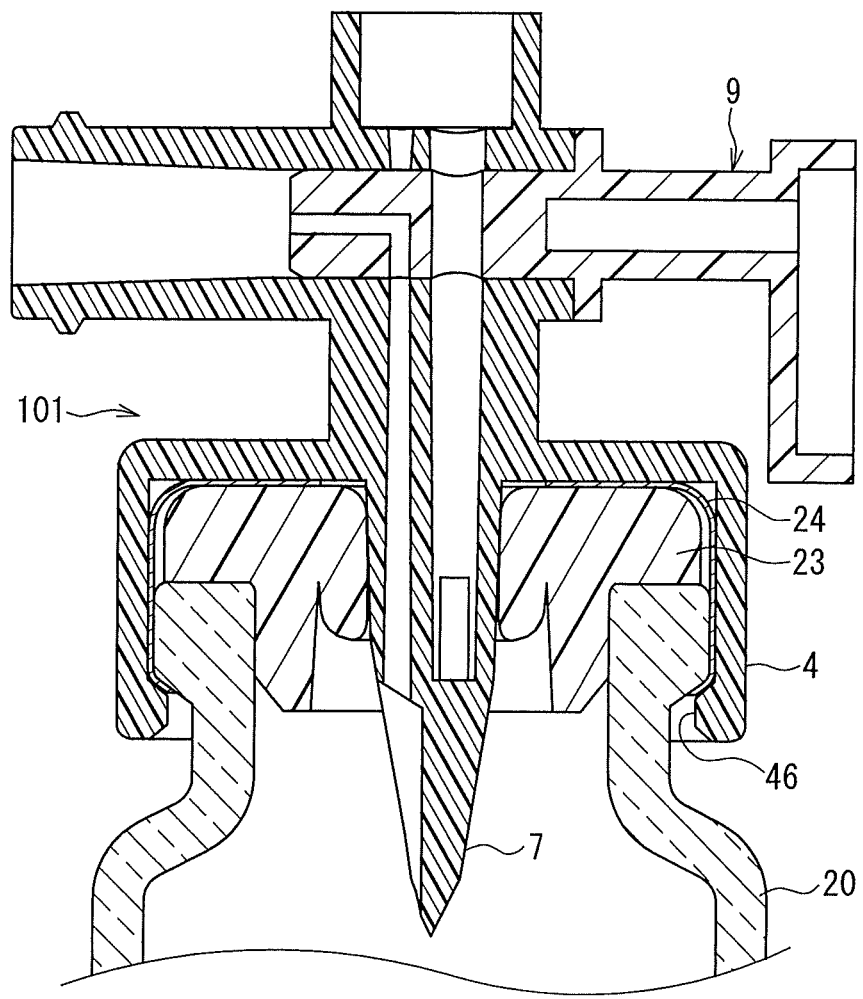
FIG. 33 is a cross-sectional view showing a state in which the second connecting portion 4 according to Embodiment 7 of the present invention has been connected to the vial 20.

FIG. 33 is a cross-sectional view showing a state in which the second connecting portion 4 has been connected to the vial 20. The inner circumferential surface of the second connecting portion 4 and the outer circumferential surface of the cap 24 of the vial 20 are fitted to each other. As shown in FIGS. 23 and 24, slits 5 are formed in a side wall portion of the second connecting portion 4 and facilitate fitting of the second connecting portion 4 to the vial 20.

In FIG. 33, the rubber stopper 23 of the vial 20 is pierced with the needle-like portion 7 that is integral with the connector main body 101. The protrusion 46 of the second connecting portion 4 is engaged with the expanded-diameter portion 47 of the vial 20, and this prevents the second connecting portion 4 from falling off the vial 20.

Moreover, unlike the first connecting portion 3, the second connecting portion 4 is not provided with a mechanism that facilitates disconnection, such as the lever locks 12. For this reason, once the second connecting portion 4 is fitted firmly to the vial 20, the second connecting portion 4 can be prevented from readily falling off the vial 20. Thus, leakage of the drug solution due to easy detachment of the vial 20 can be prevented.

Moreover, after the first connecting portion 3 has been detached from the drug solution bag 10, as shown in FIG. 30, the upright tubular portion 25 is covered with the shield 26. Therefore, leakage of the drug solution from the upright tubular portion 25 is prevented even after detachment of the first connecting portion 3 from the drug solution bag 10.

Thus, if the vial 20 is disposed of in a state in which the first connecting portion 3 has been detached from the drug solution bag 10 and the second connecting portion 4 and the vial 20 remain in the connected state, leakage of the drug in the vial 20 is prevented.

The drug leakage preventing structure as described above is particularly effective in the case where the drug in the vial 20 is a highly toxic drug such as an anticancer agent.

It should be noted that the second connecting portion 4 of the present embodiment is merely an example, and various types of connecting systems can be employed. Moreover, although the second connecting portion 4 is formed integrally with the connector main body 101, the second connecting portion 4 may be configured as a component separate from the connector main body 101 as long as a structure that prevents the second connecting portion 4 from readily falling off the connector main body 101 can be achieved.

Moreover, as described above, the connector according to Embodiments 1 to 7 can be interposed between containers to transfer a liquid. Thus, the containers to be connected to the connector are not limited to the drug solution bag and the vial, and various containers can be used to transfer a liquid between containers.

INDUSTRIAL APPLICABILITY

As described above, the connector according to the present invention can prevent easy detachment of a connected container and prevent liquid leakage from the container and, therefore, is useful as, for example, a medical connector that can be interposed between a drug solution bag and a vial to inject a pharmaceutical preparation in the vial into the drug solution bag.

REFERENCE SIGNS LIST 1, 50, 60, 70, 80, 90, 100 connector
2, 101 connector main body
3 first connecting portion
4 second connecting portion
5 slit
6 connecting port (engagement portion)
11 connecting port
7 needle-like portion
8 lever
8a leading end of lever
9 stopcock
10 drug solution bag (first container)
12 lever lock
13 claw portion
14, 39 hydrophobic filter
16 horizontal tubular portion
20 vial (second container)
23 rubber stopper
25 upright tubular portion
26, 34 shield
29 mouth portion
30 syringe
31 piston
32 cylinder
36 penetrating flow channel
37 first hole
38 third hole
46 protrusion
49 projection
51 dropper (with bellows)
54 L-shaped flow channel
55, 56 opening
58 second hole
59 fourth hole
61 dropper (ovoid)
71 first connecting portion (rotary lock)
75 recessed groove

The invention claimed is:

1. A connector that can be connected to a first container and a second container to transfer a liquid between the first container and the second container, the connector comprising:
a connector main body provided with a tubular portion and a stopcock fitted in the tubular portion so as to be rotatable around an axis of the tubular portion, one end of the tubular portion being sealed with the stopcock fitted in the tubular portion, an open portion being formed at the other end of the tubular portion, a first hole, a second hole, a third hole, and a fourth hole being formed in the connector main body;
a first connecting portion that is engageable with the first container;
a second connecting portion that is engageable with the second container;
a first flow channel formed in the stopcock that passes through the stopcock in a radial direction, and
a second flow channel formed in the stopcock that brings an opening formed on the open portion side into communication with an opening formed in a side face of the stopcock,
wherein the second connecting portion is integrally provided with an engagement portion that is engageable with the second container and a needle-like portion for piercing into the second container, and
wherein the connector is configured to switch between a first setting that brings the first hole into communication with the second flow channel in the stopcock and brings the third hole into communication with the fourth hole via the first flow channel and a second setting that brings the second hole into communication with the second flow channel in the stopcock and brings the third hole into communication with the fourth hole via the first flow channel by rotating the stopcock.

2. The connector according to claim 1,
wherein the first connecting portion comprises a releasing mechanism for releasing engagement with the first container, and
the second connecting portion does not comprise a lever releasing mechanism for releasing engagement with the second container.

3. The connector according to claim 1,
wherein the engagement portion of the second connecting portion is a hollow cylindrical connecting port that is engageable with a mouth portion of the second container, and
the connecting port has a protrusion protruding from an inner circumferential surface of the connecting port.

4. The connector according to claim 3, wherein the connecting port has a slit that is cut in a side face of the connecting port.

5. The connector according to claim 1,
wherein the first connecting portion is integrally provided with a lever lock having a claw portion that is engageable with a portion of the first container,
the lever lock doubles as a releasing mechanism for releasing engagement with the first container, and
engagement of the lever lock with the first container is released by bending the lever lock.

6. The connector according to claim 1,
wherein the first connecting portion is a rotary lock,
the rotary lock has a recessed groove that is engageable with a projection formed on the first container,
the rotary lock doubles as a releasing mechanism for releasing engagement with the first container, and
engagement between the projection and the recessed groove is released by rotating the rotary lock around an axis thereof.

7. The connector according to claim 1, further comprising a syringe that comprises a cylinder and a movable piston,
wherein a liquid is transferred between the first container and the second container by ejecting and drawing in air by moving the piston.

8. The connector according to claim 7, further comprising a hydrophobic filter, wherein air is ejected and drawn in through the hydrophobic filter.

9. The connector according to claim 1, further comprising a dropper that can expand and contract,
wherein a liquid is transferred between the first container and the second container by ejecting and drawing in air by expanding and contracting the dropper.

10. The connector according to claim 9, further comprising a hydrophobic filter,
wherein air is ejected and drawn in through the hydrophobic filter.

11. The connector according to claim 1, wherein the first connecting portion has a portion covered with a shield, wherein the shield can open and close by extension and retraction.

12. The connector according to claim 1,
wherein the first connecting portion and the second connecting portion are provided in the connector main body, connecting ports are formed in the first and the second connecting portions,
the first and the third holes are in communication with a space in the first connecting portion, and
the second and the fourth holes are in communication with a space on a connecting port side of the second connecting portion.

13. The connector according to claim 12, wherein the first connecting portion comprises a lever lock that is integral with the connecting port formed in the first connecting portion.

14. The connector according to claim 12, wherein the second connecting portion has a protrusion protruding from an inner circumferential surface of the connecting port formed in the second connecting portion.

15. The connector according to claim 12, wherein the first connecting portion has a portion covered with a shield, wherein the shield can open and close by extension and retraction.

16. The connector according to claim 1, wherein a graduated syringe comprising a cylinder and a movable piston is integrally formed on the other end side of the tubular portion.

17. The connector according to claim 1,
wherein a lever extended from the stopcock is formed on the stopcock, and
the lever is disposed in such a manner that:
when the stopcock is set to the first setting that brings the first hole into communication with the second flow channel in the stopcock, a leading end of the extended lever points to an external space side communicating with the first hole, and
when the stopcock is set to the second setting that brings the second hole into communication with the second flow channel in the stopcock, the leading end of the extended lever points to an external space side communicating with the second hole.

18. The connector according to claim 1, wherein a hydrophobic filter is provided in at least one of the third hole, the penetrating flow channel, and the fourth hole.

* * * * *